(12) United States Patent
Wilson et al.

(10) Patent No.: US 10,973,849 B2
(45) Date of Patent: Apr. 13, 2021

(54) RHENIUM COMPLEXES AND METHODS OF USE FOR TREATING CANCER

(71) Applicant: CORNELL UNIVERSITY, Ithaca, NY (US)

(72) Inventors: Justin Wilson, Ithaca, NY (US); Kevin Knopf, Kensington, CT (US); Sierra Marker, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/311,961

(22) PCT Filed: Jun. 23, 2017

(86) PCT No.: PCT/US2017/038972
§ 371 (c)(1),
(2) Date: Dec. 20, 2018

(87) PCT Pub. No.: WO2017/223428
PCT Pub. Date: Dec. 28, 2017

(65) Prior Publication Data
US 2019/0175645 A1 Jun. 13, 2019

Related U.S. Application Data

(60) Provisional application No. 62/354,209, filed on Jun. 24, 2016.

(51) Int. Cl.
*A61K 33/24* (2019.01)
*A61K 31/555* (2006.01)
*A61P 35/00* (2006.01)

(52) U.S. Cl.
CPC ............ *A61K 33/24* (2013.01); *A61K 31/555* (2013.01); *A61P 35/00* (2018.01)

(58) Field of Classification Search
CPC ........ A61K 33/24; A61K 31/555; A61P 35/00
See application file for complete search history.

(56) References Cited

U.S. PATENT DOCUMENTS

| | | | |
|---|---|---|---|
| 7,321,027 B2 | 1/2008 | Mahmood et al. | |
| 8,685,369 B2 | 4/2014 | Babich et al. | |
| 8,987,491 B2 | 3/2015 | Collery et al. | |
| 2007/0071672 A1 | 3/2007 | Alberto et al. | |
| 2008/0025915 A1 | 1/2008 | Babich et al. | |
| 2015/0299233 A1 | 10/2015 | Lippard et al. | |

OTHER PUBLICATIONS

International Search Report and Written Opinion dated Sep. 13, 2017 issued in PCT/US17/38972.
Andrews M. et al., "A luminescent rhenium(I) complex of 2,7-dimethyl-1,8-naphthyridine: synthesis, spectroscopy and X-ray crystal structure", Transition Met Chem, (2009), 34, pp. 493-497 DOI 10.1007/s11243-009-9221-0.
Collery P. et al., "Uptake and Efflux of Rhenium in Cells Exposed to Rhenium Diseleno-Ether and Tissue Distribution of Rhenium and Selenium After Rhenium Diseleno-Ether Treatment in Mice", Anticancer Research, (2014), 34, pp. 1679-1690.
Collery P. et al., "Antitumor activity of a rhenium (I)-diselenoether complex in experimental models of human breast cancer", Invest New Drugs, (2015), 33, pp. 848-860 DOI 10.1007/s10637-015-0265-z.
Koike K. et al., "Mechanism of the Photochemical Ligand Substitution Reactions of fac-[Re(bpy)(CO)3(PR3)]+ Complexes and the Properties of Their Triplet Ligand-Field Excited States", J. Am. Chem. Soc., (2002), 124, pp. 11448-11455.
Leonidova A. et al., "Underestimated Potential of Organometallic Rhenium Complexes as Anticancer Agents", ACS Chem. Biol., (2014), 9, pp. 2180/2193 dx.doi.org/10.1021/cb500528c.
Leonidova A. et al., "Enhanced Cytotoxicity through Conjugation of a "Clickable" Luminescent Re(I) Complex to a Cell-Penetrating Lipopeptide", ACS Med. Chem. Lett., (2014), 5, pp. 809-814 dx.doi.org/10.1021/ml500158w.
Leonidova A. et al., "Towards cancer cell-speci!c phototoxic organometallic rhenium(I) complexes", Dalton Trans., (2014), 43, pp. 4287-4294 DOI: 10.1039/c3dt51817e.
Ma D-L. et al., "DNA Binding and Cytotoxicity of Ruthenium(II) and Rhenium(I) Complexes of 2-Amino-4-phenylamino-6-(2-pyridyl)-1,3,5-triazine", Inorg. Chem., (2007), 46, pp. 740-749 DOI: 10.1021/ic061518s.
Medley J. et al., "DNA-binding and cytotoxic efficacy studies of organorhenium pentylcarbonate compounds", Mol. Cell Biochem., (2015), 398, pp. 21-30 DOI 10.1007/s11010-014-2201-5.

(Continued)

*Primary Examiner* — Sahar Javanmard
(74) *Attorney, Agent, or Firm* — Scully, Scott, Murphy & Presser, P.C.

(57) ABSTRACT

A composition comprising the following structure: (formula I) wherein Re represents a rhenium ion having a +1 charge; (formula II) represents an uncharged bidentate bicyclic ligand bonded to the rhenium (Re) by two ring nitrogen (N) atoms; and L is a neutral ligand independently selected from CO and neutral phosphine molecules, wherein at least one of the L groups is a CO molecule; and X⁻ represents a non-coordinating monovalent anion; wherein (formula II) is unsubstituted or substituted on any of its two rings, and said neutral phosphine molecule may or may not contain a phosphorus atom as a ring phosphorus atom; provided that, if (formula II) is unsubstituted, then one or two of said L groups are selected from said neutral phosphine molecules, with the provision that at least one of the neutral phosphine molecules has a phosphorus atom as a ring phosphorus atom. Methods for treating cancer by administering the above complex are also disclosed.

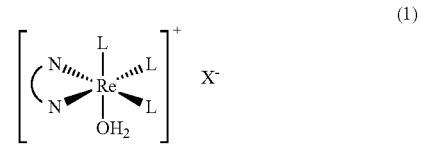

(I)

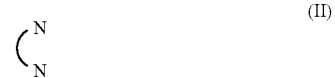

(II)

28 Claims, No Drawings

(56) References Cited

OTHER PUBLICATIONS

Morimoto T. et al., "CO2 Capture by a Rhenium(I) Complex with the Aid of Triethanolamine", J. Am. Chem. Soc., (2013), 135, pp. 16825-16828 dx.doi.org/10.1021/ja409271s.

Oriskovich T.A. et al., "Luminescent Labels for Purine Nucleobases: Electronic Properties of Guanine Bound to Rhenium(I)", Inorganic Chemistry, (1995), 35, pp. 1629-1631.

Orsa D.K. et al., "Cytotoxic Effects of Rhenium (I) Carbonyl Complexes on Prostate Cancer Cell Lines", Handbook of Prostate Cancer Cell Research, Chapter 9, (2009), pp. 323-362.

Parson C. et al., "The effect of novel rhenium compounds on lymphosarcoma, PC-3 prostate and myeloid leukemia cancer cell lines and an investigation on the DNA binding properties of one of these compounds through electronic spectroscopy", J. Bioprocess Biotech, (2014), 4, pp. 1-12.

Parson C. et al., "Anticancer Properties of Novel Rhenium Pentylcarbanato Compounds against MDA-MB-468 (HTB-132) Triple Node Negative Human Breast Cancer Cell Lines", British Journal of Pharmaceutical Research, (2014), 4(3), pp. 362-367.

Pierri A.E. et al., "A Luminescent and Biocompatible PhotoCORM", J. Am. Chem. Soc., (2012), 134, pp. 18197-18200 dx.doi.org/10.1021/ja3084434.

Ragone F. et al., "Water-Soluble (Pterin)rhenium(I) Complex: Synthesis, Structural Characterization, and Two Reversible Protonation-Deprotonation Behavior in Aqueous Solutions", Eur. J. Inorg. Chem., (2012), pp. 4801-4810 DOI: 10.1002/ejic.201200681.

Suntharalingam K. et al., "Necroptosis-Inducing Rhenium(V) Oxo Complexes", J. Am. Chem. Soc., (2015), 137, pp. 2967-2974 DOI: 10.1021/ja511978y.

Takeda H. et al., "Enhanced Photocatalysis of Rhenium(I) Complex by Light-Harvesting Periodic Mesoporous Organosilica", Inorg. Chem., (2010), 49, pp. 4554-4559 DOI: 10.1021/ic1000914.

Wilson J.J. "Rhenium as an Alternative to Platinum? Value-Added Metalloanticancer Agents", CanBIC 6 Presentation, May 25, 2017, Parry Sound, Ontario, Canada.

Zhao F. et al., "A rhenium(I) complex with indolyl-containing ligand: Synthesis, photophysical properties and theoretical studies", Inorganica Chimica Acta, (2012), 387, pp. 100-105 doi:10.1016/j.ica.2012.01.001.

Zobi F. et al., "Guanine and Plasmid DNA binding of Mono- and Trinuclear fac-[Re(CO)3]+ Complexes with Amino Acid Ligands", ChemBioChem, (2005), 6, pp. 1397-1405 DOI: 10.1002/cbic.200400453.

Zobi F. et al., "Toward Novel DNA Binding Metal Complexes: Structure and Basic Kinetic Data of [M(9MeG)2(CH3OH)(CO)3]+ (M ) 99Tc, Re)", Inorg. Chem., (2003), 42, pp. 2818-2820 DOI: 10.1021/ic030028m.

RHENIUM COMPLEXES AND METHODS OF USE FOR TREATING CANCER

CROSS REFERENCE TO RELATED APPLICATION

This application claims the benefit of priority from U.S. Provisional Application No. 62/354,209, filed on Jun. 24, 2016.

FIELD OF THE INVENTION

The invention relates generally to rhenium complexes and methods for treating cancer by administering the rhenium complex to a subject having cancer. The invention is more particularly directed to rhenium(I) complexes coordinated to neutral ligands and their use in treating various cancers, particularly platinum-resistant cancers, or in particular, ovarian cancer.

BACKGROUND OF THE INVENTION

Many cancers, such as ovarian cancer, are currently being treated with platinum-based chemotherapeutic agents, such as cisplatin or carboplatin. Although the platinum-based agents have significantly contributed to the treatment of cancer, they have several limitations, including susceptibility to relapse and platinum resistance. Moreover, the broad cytotoxicity of the platinum agents often results in substantial side effects.

The chemotherapeutic drug, cisplatin, is used in over 50% of all cases of cancer. This cytotoxic agent is used as the first-line treatment for several cancer types, including testicular and ovarian cancers. Despite its clinical success, it is limited by toxic side effects, and a decreased efficacy due to both inherent and acquired resistance of tumor cells to this drug. The design of improved agents, capable of circumventing cisplatin-resistance, is needed.

Of the cancers, there is a particular need for improved treatment of ovarian cancer. Ovarian cancer is the fifth most common cancer-related death in women (Siegel, R., et al. *Cancer Statistics, 2012, CA. Cancer J. Clin.*, 2012, 62, 10-29). Treatment is manageable at early stages of the disease using the platinum-based chemotherapeutic agents, cisplatin and carboplatin (Raja, F. A., et al. Optimal First-Line Treatment in Ovarian Cancer, *Ann. Oncol.*, 2012, 23, x118-x127). However, relapse is common and has a substantially poorer prognosis, with median survival times between 12-24 months (Armstrong, D. K., Relapsed Ovarian Cancer: Challenges and Management Strategies for a Chronic Disease, *Oncologist*, 2002, 7, 20-28).

Platinum-based drugs have several limitations for treating relapsed ovarian cancer. For example, the relapsed tumors are frequently platinum-resistant, rendering cisplatin and carboplatin treatments ineffective (Agarwal, R., et al. Ovarian Cancer: Strategies for Overcoming Resistance to Chemotherapy, *Nat. Rev. Cancer*, 2003, 3, 502-516) and the broad cytotoxicity of the platinum agent can give rise to significant side effects (Florea, A.-M., et al. Cisplatin as an Anti-Tumor Drug: Cellular Mechanisms of Activity, Drug Resistance and Induced Side Effects, *Cancers*, 2011, 3, 1351-1371). Furthermore, direct in vivo or in vitro imaging of the distribution of the platinum drugs is generally not possible using conventional methods. Drugs or drug candidates that bear such imaging modalities (i.e., theragnostic agents) enable the real-time evaluation of drug response and distribution, facilitating the evaluation of patient dosage and response. New chemotherapeutic agents that overcome the treatment limitations of the platinum drugs and simultaneously serve as theragnostic agents would greatly benefit the treatment of various cancers, particularly ovarian cancer.

SUMMARY OF THE INVENTION

In a first aspect, the instant disclosure is directed to compositions containing a rhenium (I) complex in which the rhenium (I) is bonded to all neutral (uncharged) ligands, including (i) a bidentate bicyclic ligand bonded to the rhenium by two ring nitrogen atoms, (ii) at least one carbonyl (CO) ligand (e.g., one, two, or up to three CO ligands), (iii) an axial water ($H_2O$) molecule, and optionally, (iv) one or two phosphine ligands that replace one or two CO molecules. The bidentate ligand is typically heteroaromatic and contains at least two ring nitrogen atoms that coordinate to the rhenium(I), e.g., a ligand having a bipyridyl, phenanthryl, or naphthyridyl core structure. In the complex, the rhenium(I) is charge balanced by a non-coordinating monovalent anion, such as $SO_3CF_3^-$, $PF_6^-$, tosylate, $SbF_6^-$, borate anions, $AsF_6^-$, $ClO_4^-$, and carborane anions. As halide anions (e.g., $Cl^-$) are not neutral ligands and may also coordinate to the rhenium(I), they are excluded as a neutral ligand and generally also excluded as an anion.

In more specific embodiments, the rhenium complexes have the following structure:

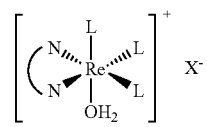

(1)

In Formula (1), Re represents a rhenium ion having a +1 charge;

represents an uncharged bidentate bicyclic ligand bonded to the rhenium (Re) by two ring nitrogen (N) atoms; and L is a neutral ligand independently selected from CO and neutral phosphine molecules, wherein at least one of the L groups is a CO molecule; and $X^-$ represents a non-coordinating monovalent anion; wherein:

is unsubstituted on any of its two rings, or

is substituted on at least one of its two rings with at least one of the following substituents: (i) hydrocarbon groups (R) containing 1-6 carbon atoms; ii) —OR' groups; (iii) —C(O) OR' groups; (iv) —OC(O)R' groups; (v) —C(O)R' groups;

(vi) —NR'₂ groups; (vii) —C(O)NR'₂ groups; (viii) —NR'C(O)R' groups; (ix) halogen atoms, and (x) —CN groups, wherein the hydrocarbon groups (R) optionally include one or more heteroatoms selected from oxygen, nitrogen, and sulfur, and R' is independently selected from hydrogen atoms and hydrocarbon groups (R); and the neutral phosphine molecule either contains a phosphorus atom as a ring phosphorus atom or does not contain a phosphorus atom as a ring phosphorus atom. In some embodiments, a provision is included that, if

is unsubstituted, then one or two of the L groups are selected from the neutral phosphine molecules, with the further provision that at least one of the neutral phosphine molecules has a phosphorus atom as a ring phosphorus atom.

In a second aspect, the instant disclosure is directed to a method for treating cancer in a subject by administering to the subject a pharmaceutically effective amount of a rhenium complex according to Formula (1), as described above. Typically, the rhenium complex is administered as a solution that contains the rhenium complex dispersed in a pharmaceutically acceptable carrier. In some embodiments, the cancer is a platinum-resistant cancer. The cancer can be, for example, ovarian cancer, cervical cancer, testicular cancer, prostate cancer, breast cancer, lung cancer, mesothelioma, squamous cell cancer, bladder cancer, lymphatic cancer, esophageal cancer, stomach cancer, gastrointestinal cancer, head-and-neck cancer, skin cancer, and pancreatic cancer.

The above-described rhenium complex and its use in the treatment of cancer represents an advance in the field of cancer treatment by providing an efficacious alternative to platinum-based agents. The alternatives described herein are based on rhenium(I) complexes instead of platinum complexes. The complexes described herein have surprisingly been found herein to have at least the potency (i.e., level of cytotoxicity) or even greater potency than cisplatin and/or other platinum-based drugs of the art in the treatment of cancer. In addition, the complexes described herein have surprisingly been found herein to exhibit effective anticancer activity in cisplatin-resistant cell lines. Moreover, the complexes described herein have been surprisingly found herein to possess a significantly lower or substantially no toxicity, and hence, a reduced or substantially imperceptible level of side effects, than cisplatin and/or other platinum-based drugs of the art. Still further, by virtue of the inherent luminescence possessed by the rhenium(I) ion, the complexes described herein advantageously permit imaging of the rhenium complex in a living organism or intracellularly, which can be used in determining the biodistribution and patient dosage-response profile of the complex.

DETAILED DESCRIPTION OF THE INVENTION

In a first aspect, the instant disclosure is directed to rhenium(I) complexes and compositions containing these complexes. The term "rhenium(I)" refers to a rhenium ion having a +1 charge. The rhenium(I) ion is hexa-coordinate and bound to only neutral (uncharged) ligands. The term "ligand" refers to a molecule that engages in a coordination bond to the rhenium(I) ion. Two of the six coordination sites of the rhenium(I) are occupied by a bidentate bicyclic ligand that binds to the rhenium(I) by two ring nitrogen atoms. A third coordination site of the rhenium(I) is occupied by an axial water molecule. A fourth coordination site of the rhenium(I) is occupied by a CO molecule. The remaining two coordination sites of the rhenium(I) are occupied by one or two CO molecules and/or one or two phosphine molecules. The term "axial," as used herein, refers to a coordination site on the rhenium(I) coordination sphere that is perpendicular to the plane of the bidentate bicyclic ligand. As the ligands are neutral, the rhenium(I)-ligand coordination sphere has a +1 charge. For purposes of the present invention, the counteranion is non-coordinating, and typically monovalent (i.e., having a charge of −1).

In more specific embodiments, the rhenium(I) complex has the following structure:

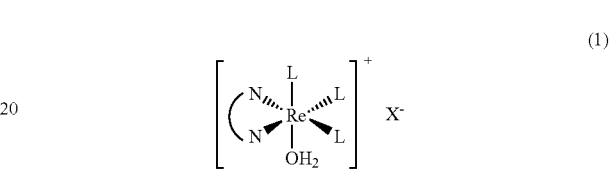

(1)

In Formula (1) above,

represents an uncharged bidentate bicyclic ligand containing two ring nitrogen atoms that coordinate to the rhenium. The term "uncharged" indicates that the bidentate bicyclic ligand is not charged (i.e., anionic or cationic) either inherently in the atoms making the core ring structure or as groups appended to the core ring structure. The term "bidentate" indicates that the ligand binds to the rhenium in two of the coordination sites of the rhenium, and more specifically, via two ring nitrogen atoms present in the bidentate bicyclic ligand. The term "bicyclic" indicates that the ligand contains two rings bonded to each other, either by a single covalent bond or as a fused ring system. In some embodiments,

possesses a saturated bicyclic ring system, e.g., 2,2'-bipiperidine. In other embodiments,

possesses an unsaturated bicyclic ring system, which may be an aliphatic bicyclic ring system or aromatic (i.e., heteroaromatic) bicyclic ring system, e.g., a bipyridine, phenanthroline, or naphthyridine ring system.

In some embodiments,

is unsubstituted on both of its two rings. The term "unsubstituted" means that only hydrogen atoms are present on (i.e., bound to) ring carbon atoms. In other embodiments,

is substituted on one or both rings, with one or more substituents. The term "substituted" means that at least one substituent (atom or group) other than a hydrogen atom is present on at least one of the ring carbon atoms. The substituent(s) can be independently selected from, for example: (i) hydrocarbon groups (R) containing 1-6 carbon atoms; ii) —OR' groups; (iii) —C(O)OR' groups; (iv) —OC(O)R' groups; (v) —C(O)R' groups; (vi) —NR'$_2$ groups; (vii) —C(O)NR'$_2$ groups; (viii) —NR'C(O)R' groups; (ix) halogen atoms, and (x) —CN groups, wherein R' is independently selected from hydrogen atoms and hydrocarbon groups (R).

The hydrocarbon group (also denoted by the group R) generally contains at least one and up to six carbon atoms. In different embodiments, the hydrocarbon group independently contains one, two, three, four, five, or six carbon atoms, or a number of carbon atoms within a range bounded by any of the above carbon numbers. Generally, if a carbonyl (C=O) group is present in the hydrocarbon group, the carbon in the carbonyl group is not counted as part of the total carbon number, unless otherwise specified. Thus, R as —C(O)(CH$_2$)$_5$CH$_3$, —C(O)O(CH$_2$)$_5$CH$_3$, or —C(O)NH(CH$_2$)$_5$CH$_3$ would be considered as having six carbon atoms, unless otherwise specified. Moreover, in the case where R is a cyclic hydrocarbon having three, four, five, or six ring carbon atoms, the cyclic hydrocarbon may or may not be substituted with one, two, three, or four methyl groups. Thus, the potential exists for a cyclic hydrocarbon group to possess up to ten carbon atoms. The hydrocarbon group can be saturated or unsaturated, straight-chained or branched, and cyclic or acyclic.

In a first set of embodiments, one or more of the hydrocarbon groups (R) are saturated and straight-chained, i.e., straight-chained alkyl groups. Some examples of straight-chained alkyl groups include methyl, ethyl, n-propyl, n-butyl, n-pentyl, and n-hexyl groups.

In a second set of embodiments, one or more of the hydrocarbon groups (R) are saturated and branched, i.e., branched alkyl groups. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, wherein the "1-yl" suffix represents the point of attachment of the group.

In a third set of embodiments, one or more of the hydrocarbon groups (R) are saturated and cyclic, i.e., cycloalkyl groups. Some examples of cycloalkyl groups include cyclopropyl, 1-methylenecyclopropyl (i.e., with presence of a methylene linker), 2-methylcycloprop-1-yl, 2,3-dimethylcycloprop-1-yl, cyclobutyl, 1-methylenecyclobutyl, 2-methylcyclobut-1-yl, 2,4-dimethylcyclobut-lyl, cyclopentyl, 1-methylenecyclopentyl, 2-methylcyclopent-1-yl, 2,5-dimethylcyclopent-1-yl, 3,4-dimethylcyclopent-1-yl, cyclohexyl, 1-methylenecyclohexyl, 2-methylcyclohex-1-yl, 2,6-dimethylcyclohex-1-yl, and 3,5-dimethylcyclohex-1-yl groups.

In a fourth set of embodiments, one or more of the hydrocarbon groups (R) are unsaturated and straight-chained. The unsaturation occurs by the presence of one or more carbon-carbon double bonds (i.e., straight-chained olefinic or alkenyl groups) and/or one or more carbon-carbon triple bonds (i.e., straight-chained alkynyl groups). Some examples of straight-chained olefinic groups include vinyl, propen-1-yl (allyl), 3-buten-1-yl (CH$_2$=CH—CH$_2$—CH$_2$—), 2-buten-1-yl (CH$_2$—CH=CH—CH$_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, and 1,3,5-hexatrien-1-yl. Some examples of straight-chained alkynyl groups include ethynyl and propargyl (2-propynyl) groups.

In a fifth set of embodiments, one or more of the hydrocarbon groups (R) are unsaturated and branched, i.e., branched alkenyl or alkynyl groups. Some examples of branched alkenyl groups include propen-2-yl (CH$_2$=C.—CH$_3$), 1-buten-2-yl (CH$_2$=C.—CH$_2$—CH$_3$), 1-buten-3-yl (CH$_2$=CH—CH.—CH$_3$), 1-propen-2-methyl-3-yl (CH$_2$=C(CH$_3$)—CH$_2$—), 1-penten-4-yl, 1-penten-3-yl, 1-penten-2-yl, 2-penten-2-yl, 2-penten-3-yl, 2-penten-4-yl, and 1,4-pentadien-3-yl, wherein the dot in any of the foregoing groups indicates a point of attachment.

In a sixth set of embodiments, one or more of the hydrocarbon groups (R) are unsaturated and cyclic, i.e., cycloalkenyl groups. The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, 2-methylphenyl (o-tolyl), 3-methylphenyl (m-tolyl), 4-methylphenyl (p-tolyl), 2,6-dimethylphenyl, 3,5-dimethylphenyl, 3,4,5-trimethylphenyl, 2,3,5,6-tetramethylphenyl, 2-methylbenzyl, 3-methylbenzyl, 4-methylbenzyl, 2,6-dimethylbenzyl, 3,5-dimethylbenzyl, and 3,4,5-trimethylbenzyl groups.

One or more of the hydrocarbon groups (R) may (i.e., optionally) include one or more heteroatoms, which are non-carbon non-hydrogen atoms. Some examples of heteroatoms include oxygen (O), nitrogen (N), sulfur (S), and halogen (halide) atoms. Some examples of halogen atoms include fluorine, chlorine, bromine, and iodine.

In some embodiments, the heteroatom inserts between at least two carbon atoms, i.e., as a —O—, —NR'—, or —S— linker (as in a —C—O—C— ether, —C—S—C— thioether, —C—N(R')—C-tertiary amine, or —C=N—C— imine linkages), wherein the shown carbon atom in each case can be considered part of a hydrocarbon group R described above, and R' independently represents hydrogen atom or any of the hydrocarbon groups (R) described above. A heteroatom-containing group may be derived by replacing one or more hydrogen and/or carbon atoms or C—H or CH$_2$ groups in a hydrocarbon group (R) with one or more heteroatoms, and/or by inserting one or more heteroatoms between carbon atoms of the hydrocarbon group (R). Some examples of heteroatom-containing groups include halogen-substituted groups (e.g., —CH$_2$F, —CHF$_2$, and —CF$_3$), carbonyl-containing groups (e.g., —C(O)R', which includes ketone and aldehyde groups), amino groups (—NR'$_2$), hydroxy and alkoxy groups (—OR'), carboxy-containing groups (—C(O)OR' or —OC(O)R'), carboxamide-containing groups (—C(O)NR'$_2$ or —N(R')C(O)R'), urea-containing groups (—NR'—C(O)—NR'$_2$), carbamate-containing groups (—NR'—C(O)—OR' or —OC(O)—NR'$_2$), nitrile (CN), sulfonyl-containing groups (—S(O)$_2$R'), and sulfinyl-containing groups (—S(O)R'), wherein R' independently represents hydrogen atom or any of the hydrocarbon groups (R) described above. For example, —C(O)OR' includes carboxylic acid (—C(O)OH) and carboxylic ester (—C(O)OR), and —OR' includes hydroxy (OH) and alkoxy (OR), where R is selected from any of the hydrocarbon groups described above. Other heteroatom-containing groups made only of heteroatoms (e.g., nitro, i.e., NO$_2$) are also considered herein. Generally, the heteroatoms, if present on an R group, do not engage in additional coordination to the Re. Thus, generally, the heteroatoms, if present on an R group, are non-coordinating to the Re. For this reason, amino-containing groups (e.g., —NR'$_2$ or —C(O)NR'$_2$ groups) are generally not included in an R group of a ligand coordinated to the Re. Such groups also have the propensity to form coordination polymers of Re, which are not considered here.

As discussed above, in some embodiments,

in Formula (1) is substituted with at least one substituent selected from: (i) hydrocarbon group (R) containing 1-6 carbon atoms; ii) —OR' groups; (iii) —C(O)OR' groups; (iv) —OC(O)R' groups; (v) —C(O)R' groups; (vi) —NR'$_2$ groups; (vii) —C(O)NR'$_2$ groups; (viii) —NR'C(O)R' groups; (ix) halogen atoms, and (x) —CN groups, wherein R' is independently selected from hydrogen atoms and hydrocarbon groups (R). Examples of hydrocarbon groups (R) have been given above. Some examples of —OR' groups, in particular, include methoxy, ethoxy, n-propoxy, isopropoxy, n-butoxy, isobutoxy, sec-butoxy, t-butoxy, n-pentoxy, isopentoxy, n-hexoxy, and isohexoxy groups.

In a particular set of embodiments,

in Formula (1) has the following structure, which contains a 2,2'-bipyridine core:

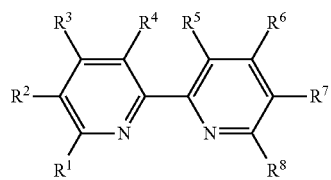

(2)

In Formula (2) above, $R^1$, $R^2$, $R^3$, $R^4$, $R^5$, $R^6$, $R^7$, and $R^8$ are independently selected from hydrogen atoms; hydrocarbon groups (R) containing 1-6 carbon atoms; —OR' groups; —C(O)OR' groups; —OC(O)R' groups; —C(O)R' groups; —NR'$_2$ groups; —C(O)NR'$_2$ groups; —NR'C(O)R' groups; halogen atoms, and —CN groups, wherein the hydrocarbon groups (R) optionally include one or more heteroatoms selected from oxygen, nitrogen, and sulfur, and R' is independently selected from hydrogen atoms and hydrocarbon groups (R). In some embodiments, $R^1$, $R^2$, $R^3$, $R^4$, $R^5$, $R^6$, $R^7$, and $R^8$ are all hydrogen atoms. In other embodiments, precisely or at least one, two, three, or four of $R^1$, $R^2$, $R^3$, $R^4$, $R^5$, $R^6$, $R^7$, and $R^8$ are not hydrogen atoms. For example, precisely or at least one, two, three, or four of $R^1$, $R^2$, $R^3$, $R^4$, $R^5$, $R^6$, $R^7$, and $R^8$ are independently hydrocarbon groups (R), or independently —OR' groups, or independently —C(O)OR' groups; or independently —OC(O)R' groups; or independently —C(O)R' groups; or independently —NR'$_2$ groups; or independently —C(O)NR'$_2$ groups; or independently —NR'C(O)R' groups; or independently halogen atoms; or independently —CN groups, or independently selected from a combination of any of the foregoing types of groups. In some embodiments, nitrogen-containing or amino-containing groups are excluded. Thus, in some embodiments, precisely or at least one, two, three, or four of $R^1$, $R^2$, $R^3$, $R^4$, $R^5$, $R^6$, $R^7$, and $R^8$ may be independently selected from hydrogen atoms; hydrocarbon groups (R) containing 1-6 carbon atoms (or more specifically, alkyl groups); —OR' groups; —C(O)OR' groups; —OC(O)R' groups; —C(O)R' groups; and halogen atoms, or selected from a sub-set of these. In some embodiments, at least one, two, three, or four of $R^1$, $R^2$, $R^3$, $R^4$, $R^5$, $R^6$, $R^7$, and $R^8$ are independently selected from hydrocarbon groups (R) containing 1-6 carbon atoms; —OR' groups; —C(O)OR' groups; —OC(O)R' groups; and —C(O)R' groups.

In some embodiments of Formula (2), at least one or two of $R^1$, $R^2$, $R^3$, and $R^4$ are not hydrogen atoms and at least one or two of $R^5$, $R^6$, $R^7$, and $R^8$ are not hydrogen atoms, e.g., at least one or two of $R^1$, $R^2$, $R^3$, and $R^4$ are independently selected from any of the groups provided above other than hydrogen, and at least one or two of $R^5$, $R^6$, $R^7$, and $R^8$ are independently selected from any of the groups provided above other than hydrogen. In more specific embodiments, at least $R^1$ and $R^8$, or at least $R^2$ and $R^7$, or at least $R^3$ and $R^6$, or at least $R^4$ and $R^5$, or a combination thereof are not hydrogen atoms and are independently selected from any of the groups provided above, i.e., independently hydrocarbon groups (R), or independently —OR' groups, or independently —C(O)OR' groups; or independently —OC(O)R' groups; or independently —C(O)R' groups; or independently —NR'$_2$ groups; or independently —C(O)NR'$_2$ groups; or independently —NR'C(O)R' groups; or independently halogen atoms, or independently —CN groups, or independently selected from two, three, four, or five of any of the foregoing types of groups. In some embodiments, at least $R^1$ and $R^8$, or at least $R^2$ and $R^7$, or at least $R^3$ and $R^6$, or at least $R^4$ and $R^5$, or a combination thereof are independently selected from hydrocarbon groups (R) containing 1-6 carbon atoms; —OR' groups; —C(O)OR' groups; —OC(O)R' groups; and —C(O)R' groups, or a subset thereof. In further specific embodiments, at least $R^1$ and $R^8$, or at least $R^2$ and R, or at least $R^3$ and $R^6$, or at least $R^4$ and $R^5$, or a combination thereof are selected from (i) straight-chained and/or branched alkyl groups (R") having 1-6 or 1-4 carbon atoms (e.g., methyl, ethyl, n-propyl, isopropyl, n-butyl, isobutyl, sec-butyl, and t-butyl), and phenyl groups, (ii) —OR" (and phenoxy) groups, (iii) —C(O)OR" groups, (iv) —OC(O)R" groups, and/or (v) —C(O)R" groups, wherein a phenyl group may replace R" in each instance, and the phenyl group may or may not contain one or more substituents, such as methyl or methoxy groups, as discussed above.

In Formula (2), any two $R^1$, $R^2$, $R^3$, $R^4$, $R^5$, $R^6$, $R^7$, and $R^8$ groups adjacent from each other may interconnect to form a ring. Moreover, the interconnection may be saturated or unsaturated. For example, $R^4$ and $R^5$ can be taken as methyl groups and the methyl groups interconnected with formation of a carbon-carbon double bond and loss of four hydrogen atoms so as to form a phenanthroline structure. Alternatively, for example, R¹ and R² may interconnect to form a benzene ring and R⁷ and R⁸ may likewise interconnect to form a benzene ring, in which case the structure of Formula (2) corresponds to a bisquinoline structure having the following structure:

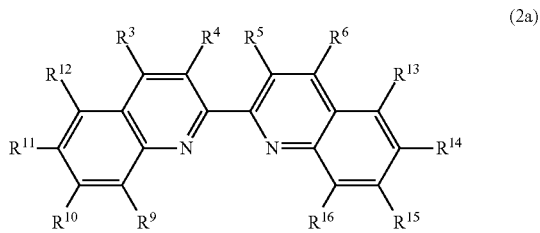

(2a)

In Formula (2a) above, $R^3$, $R^4$, $R^5$, and $R^6$ retain their definitions provided earlier above under Formula (2), and the $R^9$, $R^{10}$, $R^{11}$, $R^{12}$, $R^{13}$, $R^{14}$, $R^{15}$, and $R^{16}$ groups are independently selected from any of the groups or sub-sets thereof as provided above, e.g., independently selected from hydrogen atoms; hydrocarbon groups (R) containing 1-6 carbon atoms, or more specifically, alkyl groups R"; —OR' or —OR" groups; —C(O)OR' or —C(O)OR' groups; —OC(O)R' or —OC(O)R" groups; —C(O)R' or —C(O)R" groups; —NR'₂ groups; —C(O)NR'₂ groups; —NR'C(O)R' groups; halogen atoms, and —CN groups, or they may be independently selected from a subset thereof, particularly those groups not containing nitrogen atoms. In some embodiments, $R^3$, $R^4$, $R^5$, $R^6$, $R^9$, $R^{10}$, $R^{11}$, $R^{12}$, $R^{13}$, $R^{14}$, $R^{15}$, and $R^{16}$ groups are all hydrogen atoms. In other embodiments, one, two, three, or four of $R^3$, $R^4$, $R^5$, $R^6$, $R^9$, $R^{10}$, $R^{11}$, $R^{12}$, $R^{13}$, $R^{14}$, $R^{15}$, and $R^{16}$ groups are not hydrogen atoms and are selected from any of the non-hydrogen groups provided above, particularly those groups not containing nitrogen atoms. In more specific embodiments, only or at least $R^9$ and $R^{16}$ and/or $R^{12}$ and $R^{13}$ are not hydrogen atoms and are selected from any of the non-hydrogen groups provided above, particularly those groups not containing nitrogen atoms.

Alternatively, for example, R² and R³ in FIG. (2) may interconnect to form a benzene ring and R⁶ and R⁷ may likewise interconnect to form a benzene ring, in which case the structure of Formula (2) corresponds to a bisquinoline structure having the following structure:

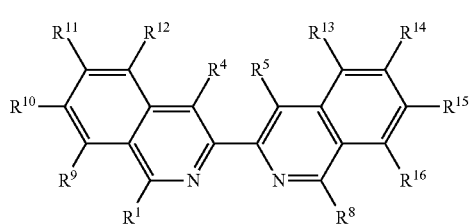

(2b)

In Formula (2b) above, $R^1$, $R^4$, $R^5$, and $R^8$ retain their definitions provided earlier above under Formula (2), and the $R^9$, $R^{10}$, $R^{11}$, $R^{12}$, $R^{13}$, $R^{14}$, $R^{15}$, and $R^{16}$ groups are defined as provided under Formula (2a). In some embodiments, $R^1$, $R^4$, $R^5$, $R^8$, $R^9$, $R^{10}$, $R^{11}$, $R^{12}$, $R^{13}$, $R^{14}$, $R^1$, and $R^{16}$ groups are all hydrogen atoms. In other embodiments, one, two, three, or four of $R^1$, $R^4$, $R^5$, $R^8$, $R^9$, $R^{10}$, $R^{11}$, $R^{12}$, $R^{13}$, $R^{14}$, $R^{15}$, and $R^{16}$ groups are not hydrogen atoms and are selected from any of the non-hydrogen groups provided above, particularly those groups not containing nitrogen atoms. In more specific embodiments, only or at least $R^1$ and $R^8$ and/or $R^9$ and $R^{16}$ and/or $R^{10}$ and $R^{15}$ and/or $R^{11}$ and $R^{14}$ and/or $R^{12}$ and $R^{13}$ are not hydrogen atoms and are selected from any of the non-hydrogen groups provided above, particularly those groups not containing nitrogen atoms.

In another particular set of embodiments,

in Formula (1) has the following structure, which contains a phenanthroline core:

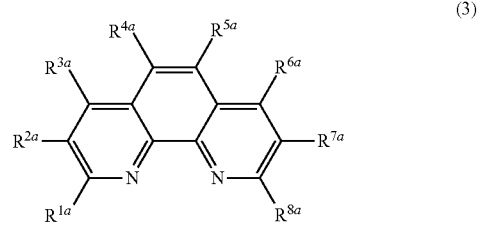

(3)

In Formula (3) above, $R^{1a}$, $R^{2a}$, $R^{3a}$, $R^{4a}$, $R^{5a}$, $R^{6a}$, $R^{7a}$, and $R^{8a}$ are independently selected from hydrogen atoms; hydrocarbon groups (R) containing 1-6 carbon atoms; —OR' groups; —C(O)OR' groups; —OC(O)R' groups; —C(O)R' groups; —NR'₂ groups; —C(O)NR'₂ groups; —NR'C(O)R' groups; halogen atoms, and —CN groups, wherein the hydrocarbon groups (R) optionally include one or more heteroatoms selected from oxygen, nitrogen, and sulfur, and R' is independently selected from hydrogen atoms and hydrocarbon groups (R). In some embodiments, $R^{1a}$, $R^{2a}$, $R^{3a}$, $R^{4a}$, $R^{5a}$, $R^{6a}$, $R^{7a}$, and $R^{8a}$ are all hydrogen atoms. In other embodiments, precisely or at least one, two, three, or four of $R^{1a}$, $R^{2a}$, $R^{3a}$, $R^{4a}$, $R^{5a}$, $R^{6a}$, $R^{7a}$, and $R^{8a}$ are not hydrogen atoms. For example, precisely or at least one, two, three, or four of $R^{1a}$, $R^{2a}$, $R^{3a}$, $R^{4a}$, $R^{5a}$, $R^{6a}$, $R^{7a}$, and $R^{8a}$ are independently hydrocarbon groups (R), or independently —OR' groups, or independently —C(O)OR' groups; or independently —OC(O)R' groups; or independently —C(O)R' groups; or independently —NR'₂ groups; or independently —C(O)NR'₂ groups; or independently —NR'C(O)R' groups; or independently halogen atoms; or independently —CN groups, or independently selected from a combination of any of the foregoing types of groups. In some embodiments, nitrogen-containing or amino-containing groups are excluded. Thus, precisely or at least one, two, three, or four of $R^{1a}$, $R^{2a}$, $R^{3a}$, $R^{4a}$, $R^{5a}R^{6a}$, $R^{7a}$, and $R^{8a}$ may be independently selected from hydrogen atoms; hydrocarbon groups (R) containing 1-6 carbon atoms (or more specifically, alkyl groups); —OR' groups; —C(O)OR' groups; —OC(O)R' groups; —C(O)R' groups; and halogen atoms, or selected from a sub-set of these. In some embodiments, at least one, two, three, or four of $R^{1a}$, $R^{2a}$, $R^{3a}$, $R^{4a}$, $R^{5a}$, $R^{6a}$, $R^{7a}$, and $R^{8a}$ are independently selected from hydrocarbon groups (R) containing 1-6 carbon atoms; —OR' groups; —C(O)OR' groups; —OC(O)R' groups; and —C(O)R' groups.

In some embodiments of Formula (3), at least one or two of $R^{1a}$, $R^{2a}$, and $R^{3a}$ are not hydrogen atoms and at least one or two of $R^{6a}$, $R^{7a}$, and $R^{8a}$ are not hydrogen atoms, e.g., at least one or two of $R^{1a}$, $R^{2a}$, and $R^{3a}$ are independently selected from any of the groups provided above other than hydrogen, and at least one or two of $R^{6a}$, $R^{7a}$, and $R^{8a}$ are independently selected from any of the groups provided above other than hydrogen. In more specific embodiments, at least $R^{1a}$ and $R^{8a}$, or at least $R^{2a}$ and $R^{7a}$, or at least $R^{3a}$ and $R^{6a}$, or at least $R^{4a}$ and $R^{8a}$, or a combination thereof are not hydrogen atoms and are independently selected from any of the groups provided above, i.e., independently hydrocarbon groups (R), or independently —OR' groups, or independently —C(O)OR' groups; or independently —OC(O)R' groups; or independently —C(O)R' groups; or independently —NR'$_2$ groups; or independently —C(O)NR'$_2$ groups; or independently —NR'C(O)R' groups; or independently halogen atoms; or independently —CN groups, or independently selected from two, three, four, or five of any of the foregoing types of groups. In some embodiments, at least $R^{1a}$ and $R^{8a}$, or at least $R^{2a}$ and $R^{7a}$, or at least $R^{3a}$ and $R^{6a}$, or at least $R^{4a}$ and $R^{8a}$, or a combination thereof are independently selected from hydrocarbon groups (R) containing 1-6 carbon atoms; —OR' groups; —C(O)OR' groups; —OC(O)R' groups; —C(O)R' groups, and halogen atoms, or a subset thereof. In further specific embodiments, at least $R^{1a}$ and $R^{8a}$, or at least $R^{2a}$ and $R^{7a}$, or at least $R^{3a}$ and $R^{6a}$ or at least $R^{4a}$ and $R^{8a}$, or a combination thereof are selected from (i) straight-chained and/or branched alkyl groups (R") having 1-6 or 1-4 carbon atoms (e.g., methyl, ethyl, n-propyl, isopropyl, n-butyl, isobutyl, sec-butyl, and t-butyl), and phenyl groups, (ii) —OR" (and phenoxy) groups, (iii) —C(O)OR" groups, (iv) —OC(O)R" groups, and/or (v) —C(O)R" groups, wherein a phenyl group may replace R" in each instance, and the phenyl group may or may not contain one or more substituents, such as methyl or methoxy groups, as discussed above.

In Formula (3), any two $R^{1a}$, $R^{2a}$, $R^{3a}$, $R^{4a}$, $R^{5a}$, $R^{6a}$, $R^{7a}$, and $R^{8a}$ groups adjacent from each other may interconnect to form a ring. Moreover, the interconnection may be saturated or unsaturated. For example, $R^{1a}$ and $R^{2a}$ may interconnect to form a benzene ring and $R^{7a}$ and $R^{8a}$ may likewise interconnect to form a benzene ring, in which case the structure of Formula (3) corresponds to a dibenzo[b,j][1,10]phenanthroline structure. Alternatively, for example, $R^{2a}$ and $R^{3a}$ may interconnect to form a benzene ring and $R^{6a}$ and $R^{7a}$ may likewise interconnect to form a benzene ring, in which case the structure of Formula (3) corresponds to a dibenzo[c,i][1,10]phenanthroline. Moreover, the interconnected portions may or may not be substituted on one or more of the ring carbon atoms by any of the groups provided above.

In another particular set of embodiments,

in Formula (1) has the following structure, which contains a 1,8-naphthyridine core:

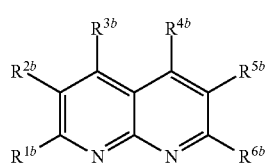

(4)

In Formula (4) above, $R^{1b}$, $R^{2b}$, $R^{3b}$, $R^{4b}$, $R^{5b}$, and $R^{6b}$ are independently selected from hydrogen atoms; hydrocarbon groups (R) containing 1-6 carbon atoms; —OR' groups; —C(O)OR' groups; —OC(O)R' groups; —C(O)R' groups; —NR'$_2$ groups; —C(O)NR'$_2$ groups; —NR'C(O)R' groups; halogen atoms, and —CN groups, wherein the hydrocarbon groups (R) optionally include one or more heteroatoms selected from oxygen, nitrogen, and sulfur, and R' is independently selected from hydrogen atoms and hydrocarbon groups (R). In some embodiments, $R^{1b}$, $R^{2b}$, $R^{3b}$, $R^{4b}$, $R^{5b}$, and $R^{6b}$ are all hydrogen atoms. In other embodiments, precisely or at least one, two, three, or four of $R^{1b}$, $R^{2b}$, $R^{3b}$, $R^{4b}$, $R^{5b}$, and $R^{6b}$ are not hydrogen atoms. For example, precisely or at least one, two, three, or four of $R^{1b}$, $R^{2b}$, $R^{3b}$, $R^{4b}$, $R^{5b}$, and $R^{6b}$ are independently hydrocarbon groups (R), or independently —OR' groups, or independently —C(O)OR' groups; or independently —OC(O)R' groups; or independently —C(O)R' groups; or independently —NR'$_2$ groups; or independently —C(O)NR'$_2$ groups; or independently —NR'C(O)R' groups; or independently halogen atoms; or independently —CN groups, or independently selected from a combination of any of the foregoing types of groups. In some embodiments, nitrogen-containing or amino-containing groups are excluded. Thus, precisely or at least one, two, three, or four of $R^{1b}$, $R^{2b}$, $R^{3b}$, $R^{4b}$, $R^{5b}$, and $R^{6b}$ may be independently selected from hydrogen atoms; hydrocarbon groups (R) containing 1-6 carbon atoms (or more specifically, alkyl groups); —OR' groups; —C(O)OR' groups; —OC(O)R' groups; —C(O)R' groups; and halogen atoms, or selected from a sub-set of these. In some embodiments, at least one, two, three, or four of $R^{1b}$, $R^{2b}$, $R^{3b}$, $R^{4b}$, $R^{5b}$ and $R^{6b}$ are independently selected from hydrocarbon groups (R) containing 1-6 carbon atoms; —OR' groups; —C(O)OR' groups; —OC(O)R' groups; and —C(O)R' groups.

In some embodiments of Formula (4), at least one or two of $R^{1b}$, $R^{2b}$, and $R^{3b}$ are not hydrogen atoms and at least one or two of $R^{4b}$, $R^{5b}$, and $R^{6b}$ are not hydrogen atoms, e.g., at least one or two of $R^{1b}$, $R^{2b}$, and $R^{3b}$ are independently selected from any of the groups provided above other than hydrogen, and at least one or two of $R^{4b}$, $R^{5b}$, and $R^{6b}$ are independently selected from any of the groups provided above other than hydrogen. In more specific embodiments, at least $R^{1b}$ and $R^{6b}$, or at least $R^{2b}$ and $R^{5b}$, or at least $R^{3b}$ and $R^{4b}$, or a combination thereof are not hydrogen atoms and are independently selected from any of the groups provided above, i.e., independently hydrocarbon groups (R), or independently —OR' groups, or independently —C(O)OR' groups; or independently —OC(O)R' groups; or independently —C(O)R' groups; or independently —NR'$_2$ groups; or independently —C(O)NR'$_2$ groups; or independently —NR'C(O)R' groups; or independently halogen atoms, or independently —CN groups, or independently selected from two, three, four, or five of any of the foregoing types of groups. In some embodiments, at least $R^{1b}$ and $R^{6b}$, or at least $R^{2b}$ and $R^{5b}$, or at least $R^{3b}$ and $R^{4b}$, or a combination thereof are independently selected from hydrocarbon groups (R) containing 1-6 carbon atoms; —OR' groups; —C(O)OR' groups; —OC(O)R' groups; and —C(O)R' groups, or a subset thereof. In further specific embodiments, at least $R^{1b}$ and $R^{6b}$, or at least $R^{2b}$ and $R^{5b}$, or at least $R^{3b}$ and $R^{4b}$, or a combination thereof are selected from (i) straight-chained and/or branched alkyl groups (R") having 1-6 or 1-4 carbon atoms (e.g., methyl, ethyl, n-propyl, isopropyl, n-butyl, isobutyl, sec-butyl, and t-butyl), and phenyl groups, (ii) —OR" (and phenoxy) groups, (iii) —C(O)OR" groups, (iv) —OC(O)R" groups, and/or (v)

—C(O)R" groups, wherein a phenyl group may replace R" in each instance, and the phenyl group may or may not contain one or more substituents, such as methyl or methoxy groups, as discussed above.

In Formula (4), any two $R^{1b}$, $R^{2b}$, $R^{3b}$, $R^{4b}$, $R^{5b}$, and $R^{6b}$ groups adjacent from each other may interconnect to form a ring. Moreover, the interconnection may be saturated or unsaturated. For example, $R^{1b}$ and $R^{2b}$ may interconnect to form a benzene ring and $R^{5b}$ and $R^{6b}$ may likewise interconnect to form a benzene ring, in which case the structure of Formula (4) corresponds to a dibenzo[b,g][1,8]naphthyridine structure. Alternatively, for example, $R^{2b}$ and $R^{3b}$ may interconnect to form a benzene ring and $R^{4b}$ and $R^{5b}$ may likewise interconnect to form a benzene ring, in which case the structure of Formula (4) corresponds to a dibenzo[c,f][1,8]naphthyridine. As another example, $R^{3b}$ and $R^{4b}$ may interconnect to form a benzene ring, in which case the structure of Formula (4) corresponds to a benzo[d,e][1,8]naphthyridine (i.e., 1,9-diazaphenalene). Moreover, the interconnected portions may or may not be substituted on one or more of the ring carbon atoms by any of the groups provided above.

Reverting back to Formula (1), the three L groups are independently selected from carbon monoxide (CO) and neutral phosphine molecules (ligands). At least one of the L groups is a CO molecule. Thus, the remaining two L groups are either both CO molecules, a CO and phosphine molecule, or both phosphine molecules (or a single diphosphine molecule).

The phosphine ligand is any molecule known in the art of the general formula $PR^aR^bR^c$, i.e., of the following structure:

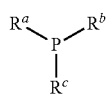

(5)

wherein $R^a$, $R^b$, and $R^c$ are independently selected from any of the hydrocarbon groups R described above, wherein one, two, or all of $R^a$, $R^b$, and $R^c$ optionally and independently include one or more heteroatoms or heteroatom-containing groups, as described above (e.g., by insertion between a C—C bond or by replacement of a hydrogen atom), provided that the heteroatoms, if present, do not form a coordination bond with the Re (i.e., only the phosphorus atom in the phosphine molecule coordinates with the Re). Each of $R^a$, $R^b$, and $R^c$ bond to the phosphorus atom by a carbon atom, i.e., $R^a$, $R^b$, and $R^c$ are all bound to the phosphorus atom by a P—C bond. The phosphine considered herein should also be a stable phosphine, i.e., it should not be reactive with water or oxygen to form a phosphine oxide or other degradation product. The phosphine should have sufficient stability to remain as a phosphine and remain bound to the Re via a phosphorus-rhenium coordination bond. Thus, generally, at least one of $R^a$, $R^b$, and $R^c$ is aromatic (e.g., phenyl) or an alkyl group having hydroxy or ether groups. More typically, $R^a$, $R^b$, and $R^c$ are not alkyl groups composed of only carbon and hydrogen, since such phosphines are typically substantially reactive with air and water.

In some embodiments, none of $R^a$, $R^b$, and $R^c$ contains a phosphorus atom. In that case, the phosphine molecule according to Formula (5) contains only one phosphorus atom and is a mono-phosphine. Some examples of mono-phosphine molecules include triphenylphosphine, tris-(o-tolyl)phosphine, tris-(p-tolyl)phosphine, tris-(o-methoxyphenyl)phosphine, tris-(m-methoxyphenyl)phosphine, tris-(p-methoxyphenyl)phosphine, and tris(hydroxymethyl)phosphine.

In other embodiments, one of $R^a$, $R^b$, and $R^c$ contains a phosphorus atom attached to hydrocarbon groups with the same type of structure provided in Formula (5) above. In that case, the phosphine molecule according to Formula (5) includes two phosphorus atoms and is a diphosphine. Some examples of diphosphine molecules include 2,2'-bis(diphenylphosphino)-1,1'-biphenyl, 2,2'-bis(dicyclohexylphosphino)-1,1'-biphenyl, ethylenebis(diphenylphosphine), 2,2'-bis[di(3,5-di-t-butylphenyl)phosphino]-6,6'-dimethoxy-1,1'-biphenyl, 2,2'-bis[bis(4-methoxy-3,5-di-t-butylphenyl)phosphino]-4,4',6,6'-tetramethoxy)-1,1'-biphenyl, 2,2'-bis(diphenylphosphino)-1,1'-binaphthyl (BINAP), 2,2'-bis(diphenylphosphino)-6,6'-dimethoxy-1,1'-biphenyl, and 1,2-bis[(2-methoxyphenyl)(phenyl)phosphino]ethane.

In some embodiments, two of $R^a$, $R^b$, and $R^c$ interconnect to form a phosphorus-containing ring. The interconnection typically includes carbon-carbon unsaturated bonds, e.g., a phosphabenze (i.e., phosphorine or phosphinine), a phosphole, or phosphaphenalene. In other embodiments, all three of $R^a$, $R^b$, and $R^c$ interconnect to form a phosphorus-containing bicyclic or higher multicyclic (e.g., adamantane) structure. In each case, the resulting phosphine contains a phosphorus atom as a ring phosphorus atom. Generally, the phosphorus-containing ring contains one or more heteroatoms other than phosphorus, e.g., ether or tertiary amine groups within the ring. Some examples of such cyclic phosphines include 1,3,5-triaza-7-phosphaadamantane (PTA) and 3,7-diacetyl-1,3,7-triaza-5-phosphabicyclo[3.3.1]nonane (DAPTA). PTA and DAPTA phosphine molecules are described in, for example, D. J. Darensbourg, et al., *Organometallics*, 2004, 23 (8), pp 1747-1754, the contents of which are herein incorporated by reference in their entirety. In some embodiments, none of $R^a$, $R^b$, and $R^c$ interconnect to form a phosphorus-containing ring. In that case, the phosphine ligand does not contains a phosphorus atom as a ring phosphorus atom.

In some embodiments, if

in any of Formulas (1), (2), (3), or (4) is unsubstituted, then one or two of the L groups in Formula (1) are selected from any of the neutral phosphine molecules described above. In more particular embodiments, if

in any of Formulas (1), (2), (3), or (4) is unsubstituted, then one or two of the L groups in Formula (1) are selected from any of the neutral phosphine molecules described above, with the further provision that at least one of the neutral phosphine molecules has a phosphorus atom as a ring phosphorus atom, as also described above.

Stated differently, if

in any of Formulas (1), (2), (3), or (4) is substituted, as described above, then one or two of the L groups in Formula (1) may be a neutral phosphine molecule that either contains a phosphorus atom as a ring phosphorus atom or does not contain a phosphorus atom as a ring phosphorus atom, as described above.

The non-coordinating monovalent anion $X^-$ in Formula (1) can be any such anions well-known in the art, provided that the anion is safe for internal administration. Some examples of the anion $X^-$ include $SO_3CF_3^-$ (i.e., OTf), $PF_6^-$, tosylate, $SbF_6^-$, borate anions, $AsF_6^-$, $ClO_4^-$, and carborane anions.

The rhenium complexes described herein can be synthesized according to methodologies and techniques well known in the art. In a typical synthesis, a rhenium carbonyl complex, e.g., $Re_2(CO)_{10}$, is reacted with one or more neutral ligands under conditions in which a portion of the CO molecules are replaced with the one or more neutral ligands. To include the anion ($X^-$), the complex may first be chlorinated to produce an intermediate rhenium chloride, and the chlorine replaced with a neutral molecule and $X^-$ by reaction with the corresponding AgX salt. See, for example, A. E. Pierri et al., *J. Am. Chem. Soc.,* 134, pp. 18197-18200, 2012, the contents of which are herein incorporated by reference in their entirety.

In another aspect, the invention is directed to pharmaceutical compositions that contain any of the above-described rhenium(I) complexes dispersed in a pharmaceutically acceptable carrier, i.e., vehicle or excipient. The complex is dispersed in the pharmaceutically acceptable carrier by either being mixed (e.g., in solid form with a solid carrier) or dissolved or emulsified in a liquid carrier. The pharmaceutical composition may or may not also be formulated together with one or more additional active ingredients or adjuvants that improve the overall efficacy of the pharmaceutical composition, particularly as relates to the treatment of cancer.

The rhenium(I) complex and carrier may be formulated into pharmaceutical compositions and dosage forms according to methods well known in the art. The pharmaceutical compositions of the present invention may be specially formulated for administration in liquid or solid form. However, as the complexes described herein are particularly suited for injection, liquid formulations suitable for injection are particularly considered herein. Nevertheless, the pharmaceutical formulation may be formulated for oral administration (e.g., as tablets, capsules, powders, granules, pastes, solutions, suspensions, drenches, or syrups); parenteral administration (e.g., by subcutaneous, intramuscular or intravenous injection as provided by, for example, a sterile solution or suspension); topical application (e.g., as a cream, ointment, or spray); intravaginal or intrarectal administration (e.g., as a pessary, cream or foam); sublingual or buccal administration; ocular administration; transdermal administration; or nasal administration.

The phrase "pharmaceutically acceptable" refers herein to those compounds, materials, compositions, and/or dosage forms which are, within the scope of sound medical judgment, suitable for administration to a subject. The phrase "pharmaceutically acceptable carrier," as used herein, refers to a pharmaceutically-acceptable vehicle, such as a liquid or solid filler, diluent, carrier, manufacturing aid (e.g., lubricant, talc magnesium, calcium or zinc stearate, or stearic acid), solvent, or encapsulating material, that serves to carry the therapeutic composition for administration to the subject. Each carrier should be "acceptable" in the sense of being compatible with the other ingredients of the formulation and physiologically safe to the subject. Any of the carriers known in the art can be suitable herein depending on the mode of administration.

Some examples of materials that can serve as pharmaceutically-acceptable excipients, particularly for liquid forms, include water; isotonic saline; pH buffering agents; sugars (e.g., lactose, glucose, sucrose, and oligosaccharides, such as sucrose, trehalose, lactose, or dextran); and antimicrobials. Other excipients, more typically used in solid dosage forms, may also be included, e.g., starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

In some embodiments, the carrier further includes a molecular or microscopic (e.g., microscale or nanoscale) sub-carrier in which the complex is loaded, either within and/or conjugated onto the surface of the sub-carrier. The sub-carrier can be composed of, for example, a biocompatible and biodegradable polymer, e.g., based on a polyhydroxyacid biopolyester or polysaccharide. The overall structure of the sub-carrier can be, a micelle, a liposome, dendrimer, nanoparticle, or porous scaffold. These and numerous other types of sub-carriers are well known in the art. The sub-carrier may function to protect the complex during transit, e.g., while in the bloodstream or while passing through the gastrointestinal tract, to release the complex closer to the target cells with lower chance of degradation. The sub-carrier may also be functionalized with one or more targeting agents that selectively target a class of cells to be treated with the complex. In particular embodiments, the targeting agent selectively targets cancer cells or specific types of cancer cells. The targeting agent can be, for example, an antibody, antibody fragment, or small molecule receptor binder.

In another aspect, the invention is directed to a method for treating cancer in a subject. In the method, the above described rhenium(I) complex, typically as a pharmaceutical formulation, is administered to the subject in a pharmaceutically effective amount to treat the cancer. The mode of administration may be any of the modes of administration used for the platinum-based drugs, such as cisplatin. The typical mode of administration for purposes of the present invention is by intravenous injection. In one embodiment, the complex is injected into the bloodstream, in which case the complex is systemically distributed through the body. In another embodiment, the complex is injected locally directly into or in the vicinity of cancerous tissue.

In the treatment, the complex is administered in a therapeutically effective amount. The effective amount of the compound to be administered can be readily determined according to methods familiar to physicians and clinicians, e.g., during pre-clinical and clinical trials. As is well known in the art, the dosage of the active ingredient(s) depends on such factors as the type and stage of the cancer, the method of administration, size of the patient, and potential side effects. Dosing is dependent on the severity and responsiveness of the cancer being treated, with the course of treatment lasting from several days to several months, or until a cure is effected or a diminution of the disease state is achieved. Optimal dosing schedules can be calculated from measurements of drug accumulation in the body of the patient. The administering physician can determine optimum dosages, dosing methodologies, and repetition rates. In different embodiments, depending on these and other factors, a suitable dosage of the active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks or months. The indicated dosage may alternatively be administered every two or three days, or per week. Alternatively, or in addition, the composition is administered until a desired change is evidenced.

The composition according to Formula (1) can be co-administered with one or more other therapeutic agents outside the scope of Formula (1). In a first instance, the co-administration is accomplished by including the complex of Formula (1) in admixture with one or more other therapeutic agents in the same pharmaceutical composition being administered. In a second instance, the co-administration can be accomplished by administering the complex of Formula (1) separately from one or more other therapeutic agents, i.e., at the same time or at different times. In particular, an additional antineoplastic (e.g., anticancer drug or adjuvant) agent may or may not be included in the treatment. Anticancer agents or adjuvants suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, inhibit protein kinase activity, block receptors for growth factors, cytokines, activating ligands, and the like. In some embodiments, the rhenium complex is administered as the sole anticancer drug.

The cancer can be any of a wide varieties of cancer, particularly those cancers for which platinum drugs are known to be useful. The claimed rhenium(I) complexes can be used as a replacement of platinum drugs for treating any such cancers, and particularly those cancers found to be or having a tendency to be resistant to platinum-based treatment. In particular embodiments, the cancer being treated is ovarian cancer, testicular cancer, prostate cancer, cervical cancer, breast cancer (e.g., triple negative breast cancer), lung cancer, mesothelioma, squamous cell cancer, colon cancer, gastrointestinal cancer, stomach cancer, pancreatic cancer, bladder cancer, esophageal cancer, head-and-neck cancer, skin cancer, brain cancer, diffuse large cell lymphoma, lymphatic cancer, follicular B cell lymphoma, lymphocytic leukemia, multiple myeloma, Burkitt's lymphoma, primary mediastinal B-cell lymphoma, Hodgkin's lymphoma, non-Hodgkin's lymphoma, mantle cell lymphoma, Kaposi's sarcoma, and Cowden's syndrome. In some embodiments, the cancer is characterized by a multidrug resistant (MDR) tumor.

The Re(I) complexes described herein are advantageously significantly cytotoxic to cancer cells while eliciting minimal or substantially no toxic side effects to normal tissue. As well known in the art, the cytotoxicity of a given drug can be expressed as an $IC_{50}$ value. Depending on the precise structure of the complex and the type of cancer being treated, the complexes described herein can exhibit an $IC_{50}$ value of up to or less than 20, 15, 10, 5, 4, 3, 2, or 1 M. The complexes described herein are further advantageous by being detectable or imageable by virtue of the inherent luminescence possessed by the rhenium(I) ion. In some embodiments, fluorescence or magnetic resonance imaging is used for imaging the distribution of rhenium in bodily tissue or to track the intracellular localization. In other embodiments, the complexes can be observed by vibrational microscopy at vibrational energies in resonance with infrared transitions in the CO ligands. Another significant advantage of the complexes described herein is their insusceptibility to resistance mechanisms, unlike the platinum-based drugs.

Examples have been set forth below for the purpose of illustration and to describe the best mode of the invention at the present time. However, the scope of this invention is not to be in any way limited by the examples set forth herein.

EXAMPLES

Preparation of Complexes of the Formula $[Re(CO)_3(N-N)(H_2O)][OTf]$

I. Preparation of Precursor Complexes of the Formula $[Re(CO)_3(N-N)Cl]$

The synthesis was adapted from the following reference: Smieja, J. M.; Kubiak, C. P. *Inorg. Chem.* 2010, 49 (20), 9283. The N—N ligand was selected from among the following seven ligands:

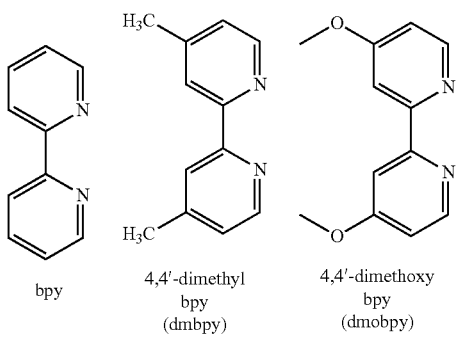

bpy 4,4'-dimethyl bpy (dmbpy)

4,4'-dimethoxy bpy (dmobpy)

-continued

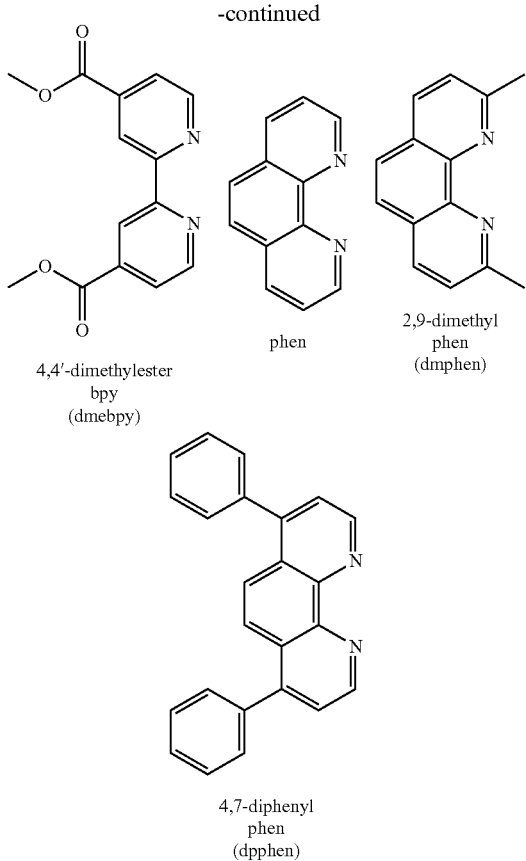

4,4'-dimethylester bpy (dmebpy)

phen 2,9-dimethyl phen (dmphen)

4,7-diphenyl phen (dpphen)

In a typical procedure, Re(CO)$_5$Cl (50 mg, 0.14 mmol) and the N—N ligand (0.14 mmol) were combined in 3 mL toluene and heated to reflux for 2 hours, except for the diphenyl phenanthroline ligand, which was refluxed for 5 hours. The precipitate was washed with pentane and diethyl ether to obtain the product as a yellow powder (orange in the case of dimethylester bipyridine and diphenyl phenanthroline). N—N=bpy (92%): 1H NMR (300 MHz, CDCl$_3$): δ (ppm)=9.10 (d, 2H); 8.20 (d, 2H); 8.09 (t, 2H); 7.56 (t, 2H). N—N=4,4'-dimethyl bpy (77%): 1H NMR (300 MHz, CDCl$_3$): δ (ppm)=8.87 (d, 2H); 7.97 (s, 2H); 7.34 (d, 2H); 2.57 (s, 6H). N—N=4,4'dimethoxy bipy (63%): 1H NMR (300 MHz, CDCl$_3$): δ (ppm)=8.82 (d, 2H); 7.54 (s, 2H); 6.97 (d, 2H); 4.01 (s, 6H). N—N=4,4'-dimethylester bipy (70%): $^1$H NMR (300 MHz, CDCl$_3$): δ (ppm)=9.27 (d, 2H); 9.11 (s, 2H); 8.21 (d, 2H); 4.08 (s, 6H). N—N=phen (78%): $^1$H NMR (300 MHz, CDCl$_3$): δ (ppm)=9.43 (d, 2H); 8.55 (d, 2H); 8.04 (s, 2H); 7.87 (dd, 2H). N—N=2,9-dimethylphen (60%): $^1$H NMR (300 MHz, dmso-d$_6$): δ (ppm)=8.79 (d, 2H); 8.17 (s, 2H); 8.08 (d, 2H); 4.05 (s, 6H). N—N=4,7-diphenyl phen (74%): $^1$H NMR (300 MHz, CDCl$_3$): δ (ppm)=9.43 (d, 2H); 8.06 (s, 2H); 7.79 (d, 2H); 7.56 (m, 10H).

II. Preparation of Complexes of the Formula [Re(CO)$_3$(N—N)(H$_2$O)][OTf]

The synthesis was generally based on the methodology disclosed in Kurz et al., *Eur. J. Inorg. Chem.* 2006, 2006 (15), 2966, but with substantial modification to obtain the axial H$_2$O ligand and OTf anion. In a typical procedure, [Re(CO)$_3$(N—N)Cl] (50 mg, 0.11 mmol) and silver triflate (28 mg, 0.11 mmol) were combined in 3 mL of acetone and heated to reflux for 2 hours. The solution was filtered to remove the silver chloride precipitate and then rotary evaporated down to an oil. 3 mL of water was added, which resulted in formation of a white precipitate. The suspension was stirred for 3 hours and then lyophilized to obtain the product as a fluffy yellow solid (orange in the case of dimethylester bipyridine). N—N=bipy (61%): IR (νCO/cm$^{-1}$): 2035, 1917. $^1$H NMR (300 MHz, MeOD-d$_4$ with D$_2$O): δ (ppm)=9.11 (d, 2H); 8.62 (d, 2H); 8.37 (t, 2H); 7.79 (t, 2H). N—N=4,4'-dimethyl bpy (35%). IR (νCO/cm$^{-1}$): 2035, 1939, 1917. $^1$H NMR (300 MHz, MeOD-d$_4$ with D$_2$O): δ (ppm)=8.92 (d, 2H); 8.44 (s, 2H); 7.59 (d, 2H); 2.62 (s, 6H). N—N=4,4'dimethoxy bipy (63%). IR (νCO/cm$^{-1}$): 2026, 1909. $^1$H NMR (300 MHz, MeOD-d$_4$ with D$_2$O): δ (ppm)=8.85 (d, 2H); 8.05 (s, 2H); 7.31 (d, 2H); 4.09 (s, 6H). N—N=4,4'-dimethylester bipy (64%). IR (νCO/cm$^{-1}$): 2030, 1913, 1726 (carbonyl on ligand). 1H NMR (300 MHz, CDCl$_3$): δ (ppm)=9.28 (d, 2H); 8.86 (s, 2H); 8.18 (d, 2H); 4.12 (s, 6H). N—N=phen (63%). IR (νCO/cm$^{-1}$): 2035, 1930, 1891. $^1$H NMR (300 MHz, CDCl$_3$): δ (ppm)=9.43 (d, 2H); 8.55 (d, 2H); 8.04 (s, 2H); 7.87 (dd, 2H). N—N=2,9-dimethylphen (43%). IR (νCO/cm$^{-1}$): 2030, 1939, 1922. $^1$H NMR (300 MHz, CDCl$_3$): δ (ppm)=8.40 (d, 2H); 7.90 (s, 2H); 7.79 (s, 2H); 3.36 (s, 6H). N—N=4,7-diphenylphen (61%). IR (νCO/cm$^{-1}$): 2022, 1939, 1930. $^1$H NMR (300 MHz, MeOD-d$_4$ with D$_2$O): δ (ppm)=9.56 (d, 2H); 8.22 (s, 2H); 8.08 (s, 2H); 7.71 (m, 10H).

Preparation of Phosphino-Rhenium (I) Complexes

Synthesis of Iodobenzene Dichloride

Iodobenzene (1.016 g) was added to a round-bottom flask covered in foil. Then 30 mL of bleach was added to the flask, stoppered, and stirred. Concentrated hydrochloric acid (10 mL) was added dropwise over the course of 15 minutes, until the solution turned yellow. After the addition of HCl was complete, the reaction mixture stirred for an additional 7 minutes. The yellow precipitate formed and was vacuum filtered and washed with abundant water and 40 mL of hexanes. The resulting yellow solid was dried on the vacuum pump overnight. Yield: 0.711 g (52%).

Synthesis of Re(CO)$_5$Cl

A mixture of dirhenium decacarbonyl, Re(CO)$_{10}$ (1.90 g, 2.91 mmol) and DCM (20 mL) was stirred until Re(CO)$_{10}$ was completely dissolved. Then iodobenzene dichloride (0.711 g, 2.59 mmol) was added to the mixture and stirred for 45 minutes to 1 hour. A white precipitate formed, which was filtered and washed with hexanes (~20-30 mL). The resulting filtrate was allowed to stir for an additional 4-5 hours to allow further precipitation of Re(CO)$_5$Cl. Yield: 1.268 g (68%). IR (KBr, cm$^{-1}$): 3435 w, 2462 w, 21567 m, 2035 s, 1958 s, 1002 w, 942 w, 912 w, 590 s, and 555 s.

Synthesis of Re(CO)$_3$(phen)Cl

A mixture of Re(CO)$_5$Cl (0.200 g, 0.55 mmol) and 1,10-phenanthroline (0.086 g, 0.55 mmol) in 12 mL of toluene was refluxed at 118° C. for 2 hours. A yellow precipitate formed and was vacuum filtered and washed with pentane (~20 mL) and then diethyl ether (~20 mL). Yield: 0.224 g. $^1$H NMR (300 MHz, DMSO-d$_6$): δ 9.45 (d, 2H), 9.00 (d, 2H), 8.34 (s, 2H), 8.12 (dd, 2H).

The following phosphine ligands were studied:

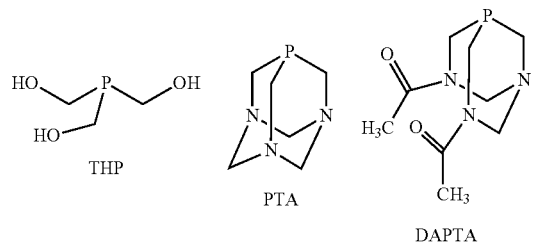

Synthesis of Re(CO)$_3$(phen)(PTA) (1)

A mixture of Re(CO)$_3$(phen)Cl (0.224 g, 0.485 mmol) and AgOTf (0.125 g, 0.485 mmol) in THF (50 mL) was refluxed at 75° C. for 3 hours in the dark. The white solid, AgCl precipitate, was removed via vacuum filtration. To the remaining yellow filtrate, 1,3,5-triaza-7-phosphaadamantane (PTA, 0.0915 g, 0.582 mmol) was added and the solution refluxed for 15 hours. The reaction mixture was allowed to cool to room temperature and then the THF was removed using rotary evaporation. The yellow solid was then purified by dissolving in minimal amount of methanol, filtering through celite, and precipitating out a yellow solid with diethyl ether. Yield: 0.298 g (84%). 1H NMR (400 MHz, MeOD-d$_4$): δ 9.53 (d, 2H), 9.00 (d, 2H), 8.34 (s, 2H), 8.15 (t, 2H), 4.33 (dd, 6), 3.64 (s, 6H). $^{19}$F{$^1$H} (400 MHz, MeOD-d$_4$, external stnd: KPF$_6$): δ −79.56. $^{31}$P{$^1$H}(400 MHz, MeOD-d$_4$, external stnd: KPF$_6$): −78.24 IR (KBr, cm$^{-1}$): 3460 m, 2910 w, 2360 m, 2330 m, 2030 s, 1940 s, 1920 s, 1430 m, 1265 m, 1244 m, 1153 m, 1029 m, 970 w, 950 w, 850 w, 726 w, 637 m, 440 w. ESI-MS (pos. ion mode, ACN:H$_2$O 70:30 and 1% formic acid): m/z 608.08745 ([M]$^+$, calcd. 608.08558). Anal. Calcd. for (1).CH$_3$OH (C$_{23}$H$_{24}$F$_3$N$_5$O$_7$PReS): C, 34.85; H, 3.02; N, 8.81. Found: C, 34.85; H, 3.02; N, 8.81.

Synthesis of Re(CO)$_3$(phen)(THP) (2)

A mixture of Re(CO)$_3$(phen)Cl (0.100 g, 0.206 mmol) and AgOTf (0.053 g, 0.206 mmol) in THF (24 mL) was refluxed at 75° C. for 3 hours in the dark. Silver chloride was removed by vacuum filtration. The remaining yellow filtrate was further refluxed after the addition of tris(hydroxymethyl)phosphine (THP) (0.038 g, 0.309 mmol) for an additional 15 hours. The reaction mixture was allowed to cool to room temperature and then THF was removed by rotary evaporation, then dissolved in a minimal amount of CH$_3$OH and filtered through celite. The crude yellow oil (0.167 g) was purified using preparatory RP-HPLC (CH$_3$OH/H$_2$O, 0-5 min (10% CH$_3$OH), 5-30 min (100% CH$_3$OH), 30-35 min (10% CH$_3$OH). Yield: 0.100 g (70%). $^1$H NMR (400 MHz, MeOD-d$_4$): δ 9.56 (d, 2H), 8.90 (d, 2H), 8.25 (s, 2H), 8.07 (t, 2H), 3.75 (t, 2H), 3.75 (s, 6H). $^{19}$F{$^1$H} (400 MHz, MeOD-d$_4$, external stnd: KPF$_6$): δ −76.37. $^{31}$P{$^1$H} (400 MHz, MeOD-d$_4$, external stnd: KPF$_6$): 2.43. IR (KBr, cm$^{-1}$) 3420 m, 3210 m, 3070 m, 2830 w, 2780 w, 2650 w, 2040 s, 1930 s, 1910 w, 1670 s, 1520 m, 1430 s, 1200 s, 1130 s, 1050 s, 888 m, 856 s, 800 s, 723 w, 635 w, 618 w, 538 m, 500 m, 483 w, 436 w. ESI-MS (pos. ion mode, ACN:H$_2$O 70:30 and 1% formic acid): m/z 575.03961 ([M]$^+$, calcd. 575.03763). Anal. Calcd. for (2) (C$_{20}$H$_{17}$F$_3$N$_2$O$_8$PRe): C, 34.94; H, 2.49; N, 4.07. Found: C, 33.93; H, 2.49; N, 3.71.

Synthesis of Re(CO)$_3$(phen)(DAPTA) (3)

A mixture of Re(CO)$_3$(phen)Cl (0.200 g, 0.42 mmol) and AgOTf (0.106 g, 0.42 mmol) in THF (47 mL) was refluxed at 75° C. for 3 hours in the dark. The white solid, AgCl precipitate, was removed via vacuum filtration. To the remaining yellow filtrate, 1,4-diacetyl-1,3,7-triaza-5-phosphabicylco[3.3.1]nonane (DAPTA, 0.113 g, 0.46 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.255 g (73%). $^1$H NMR (400 MHz, MeOD-d$_4$): δ 9.60 (d, 2H), 9.02 (d, 2H), 8.35 (s, 2H), 8.18 (t, 2H), 5.56 (d, 1.8H), 5.56 (d, 0.4H), 4.75 (d, 0.8H), 4.48 (d, 0.6H), 4.41 (d, 1H), 4.12 (dd, 0.8H), 3.93 (d, 0.8H), 3.78 (d, 1H), 3.36 (m, 2H), 3.02 (m, 1.2H), 1.94 (s, 1H), 1.91 (s, 2.8H), 1.80 (s, 2.6H). 9F{$^1$H} (400 MHz, MeOD-d$_4$, external stnd: KPF$_6$): δ −79.54. $^{31}$P{$^1$H} (400 MHz, MeOD-d$_4$, external stnd: KPF$_6$): −44.80, −48.75. IR (KBr, cm$^{-1}$): 3452 m, 2038 s, 1948 s, 1914 s, 1643 s, 1427 m, 1330 m, 1278 m, 1258 m, 1225 w, 1148 w, 1029 w, 987 w, 888 w, 849 w, 802 w, 720 w, 638 s, 540 m, 498 w, 425 w. ESI-MS (pos. ion mode, ACN:H$_2$O 70:30 and 1% formic acid): m/z 680.10846 ([M]$^+$, calcd. 680.10671). Anal. Calcd. for (3) (C$_{23}$H$_{24}$F$_3$N$_5$O$_8$PReS): C, 36.23; H, 2.92; N, 8.45. Found: C, 36.35; H, 2.79; N, 8.66.

Synthesis of Re(CO)$_2$(phen)(DAPTA)Cl (3a)

Trimethylamine-N-oxide (TMAO, 0.040 g, 0.36 mmol) was dissolved in DCM (130 mL) and MeOH (5 mL). A mixture of (3) (0.262 g, 0.32 mmol) and NEt$_4$Cl (0.919 g, 5 mmol) in DCM (105 mL) was refluxed at 50° C. and then the TMAO solution was added dropwise over the course of 1 hour and the solution turned from light yellow to dark red. The solution was refluxed for an additional 24 hours. The DCM/MeOH was removed via rotary evaporation. Then to the red solid approximately 20 mL of MeOH was added and the solid was centrifuged down. The MeOH was then removed, and this was repeated 3× with 5-10 mL MeOH. Yield: 0.150 g (94%). $^1$H NMR (400 MHz, MeOD-d$_4$): δ 9.52 (m, 2H), 8.95 (d, 2H), 8.33 (s, 2H), 8.14 (m, 2H), 5.52 (d, 0.8H), 5.06 (m, 1H), 4.89 (d, 0.8H), 4.49 (d, 1H), 4.23 (m, 0.8H), 3.93 (d, 0.8H), 3.75 (d, 0.8H), 3.32 (m, 2.4H), 3.12 (d, 1H), 1.97 (s, 0.8H), 1.90 (s, 1.3H), 1.86 (s, 1.3H). $^{31}$P{$^1$H}(400 MHz, MeOD-d$_4$, external stnd: KPF$_6$): δ −32.32, −34.72. IR (KBr, cm$^{-1}$): 3458 s, 1927 s, 1839 s, 1638 s, 1427 m, 1338 m, 1240 m, 1097 w, 1050 w, 997 w, 890 w, 855 w, 795 w, 727 w, 614 w. Anal. Calcd. for (1).CH$_3$OH (C$_{23}$H$_{24}$F$_3$N$_5$O$_7$PReS): C, 34.85; H, 3.02; N, 8.81. Found: C, 34.85; H, 3.02; N, 8.81.

Synthesis of Re(CO)$_2$(phen)(DAPTA)(H$_2$O) (3b)

(3a) (0.122 g, 0.178 mmol) was added to H$_2$O (30 mL) and, upon stirring, silver triflate (0.043 g, 0.170 mmol) was added. The solution was stirred at room temperature for 9 hours (AgCl was filtered off at 3 hours) and turned from a red to orange solution. The solution was filtered through a celite plug to remove any remaining AgCl and the water was removed by rotary evaporation to leave an orange solid. $^1$H NMR (400 MHz, D$_2$O): δ 9.53 (d, 2H), 8.89 (d, 2H), 8.25 (s, 2H), 8.08 (q, 2H), 3.99 (m, 2H), 3.59 (d, 2H), 3.29 (d, 2H), 1.55 (s, 6H). $^{19}$F{$^1$H} (400 MHz, D$_2$O, external stnd: KPF$_6$): δ −75.67. $^{31}$P{$^1$H} (400 MHz, D$_2$O, external stnd:

KPF$_6$): δ 18.34, 15.68. IR (KBr, cm$^{-1}$): 3435 s, 1936 s, 1850 s, 1673 s, 1538 m, 1428 m, 1198 s, 845 m, 726 m.

Isolation of Re(CO)$_3$(phen)(DAPTA) Photoproduct (3c)

(3) (30 mg) was irradiated with 365 nm until completion. The reaction was monitored by HPLC and the sample was purified by prep-HPLC. This resulted in an orange solid that was consistent with the synthesized product, (3b). $^1$H NMR (400 MHz, D$_2$O): δ 9.53 (d, 2H), 9.21 (d, 1.2H), 8.94 (d, 1.2H), 8.89 (d, 2H), 8.25 (s, 2H), 8.21 (s, 1.2H), 8.14 (q, 1.2H), 8.07 (q, 2H), 3.99 (m, 2H), 3.59 (d, 2H), 3.34 (d, 2H), 2.06 (s, 1H), 1.71 (s, 1H), 1.55 (s, 6H). $^{19}$F{$^1$H} (400 MHz, D$_2$O, external stnd: KPF$_6$): δ −75.67 $^{31}$P{$^1$H} (400 MHz, D$_2$O, external stnd: KPF$_6$): δ 18.27, 15.64. IR (KBr, cm$^{-1}$).

Synthesis of Re(CO)$_3$(dmphen)(PTA) (4)

A mixture of Re(CO)$_3$(dmphen)Cl (0.243 g, 0.473 mmol) and AgOTf (0.121 g, 0.473 mmol) in THF (54 mL) was refluxed at 75° C. for 3 hours in the dark. The white solid, AgCl precipitate, was removed via vacuum filtration. To the remaining yellow filtrate, 1, 3, 5-triaza-7-phosphaadamantane (PTA, 0.111 g, 0.71 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.290 g (78%). $^1$H NMR (400 MHz, MeOD-d$_4$): δ 8.80 (d, 2H), 8.23 (s, 2H), 8.13 (d, 2H), 4.25 (dd, 6H), 3.42 (s, 6H), 3.34 (s, 6H). 9F{$^1$H} (400 MHz, MeOD-d$_4$, external stnd: KPF$_6$): δ −79.56. $^{31}$P{$^1$H} (400 MHz, MeOD-d$_4$, external stnd: KPF$_6$): −79.09. IR (KBr, cm$^{-1}$): 3448 m, 3052 w, 2913 w, 2033 s, 1958 s, 1934 s, 1445 m, 1384 w, 1266 s, 1222 w, 1150 m, 1031 m, 1013 w, 972 m, 873 m, 802 w, 743 w, 638 s, 582 w, 509 w, 440 w. ESI-MS (pos. ion mode, ACN:H$_2$O 70:30 and 1% formic acid): m/z 636.11922 ([M]$^+$, calcd. 636.11743). Anal. Calcd. for (4) (C$_{24}$H$_{24}$F$_3$N$_5$O$_6$PReS): C, 36.73; H, 3.08; N, 8.92. Found: C, 36.66; H, 3.09; N, 8.98.

Synthesis of Re(CO)$_3$(dmphen)(THP) (5)

A mixture of Re(CO)$_3$(dmphen)Cl (0.209 g, 0.407 mmol) and AgOTf (0.104 g, 0.407 mmol) in THF (46 mL) was refluxed at 75° C. for 3 hours in the dark. Silver chloride was removed by vacuum filtration. The remaining yellow filtrate was further refluxed after the addition of tris(hydroxymethyl)phosphine (THP, 0.076 g, 0.612 mmol) for an additional 15 hours. The reaction mixture was allowed to cool to room temperature and then THF was removed by rotary evaporation. The crude yellow oil was purified using preparatory RP-HPLC (CH$_3$OH/H$_2$O, 0-5 min (10% CH$_3$OH), 5-50 min (100% CH$_3$OH), 50-51 min (10% CH$_3$OH)). Yield: 0.158 g (54%). 1H NMR (400 MHz, MeOD-d$_4$): δ 8.70 (d, 2H), 8.13 (s, 2H), 8.03 (d, 2H), 3.44 (s, 6H), 3.37 (s, 6H). $^{19}$F{$^1$H} (400 MHz, MeOD-d$_4$, external stnd: KPF$_6$): δ −76.35. $^{31}$P{$^1$H} (400 MHz, MeOD-d$_4$, external stnd: KPF$_6$): 6.53. IR (KBr cm$^{-1}$): 3036 m, 2837 w, 2449 w, 2044 s, 1945 s, 1909 s, 1674 s, 1594 w, 1506 w, 1442 m, 1370 w, 1202 m, 1140 m, 1043 m, 892 w, 859 m, 837 w, 800 w, 781 w, 722 w, 652 w, 619 w, 552 w, 513 w, 499 w. ESI-MS (pos. ion mode, ACN:H$_2$O 70:30 and 1% formic acid): m/z 603.07053 ([M]$^+$, calcd. 603.06947). Anal. Calcd. for (5) (C$_{22}$H$_{21}$F$_3$N$_2$O$_8$PRe): C, 36.93; H, 2.96; N, 3.91. Found: C, 36.03; H, 2.90; N, 3.77.

Synthesis of Re(CO)$_3$(dmphen)(DAPTA) (6)

A mixture of Re(CO)$_3$(dmphen)Cl (0.232 g, 0.451 mmol) and AgOTf (0.116 g, 0.51 mmol) in THF (54 mL) was refluxed at 75° C. for 3 hours in the dark. The white solid, AgCl precipitate, was removed via vacuum filtration. To the remaining yellow filtrate, 1,4-diacetyl-1,3,7-triaza-5-phosphabicylco[3.3.1]nonane (DAPTA, 0.144 g, 0.59 mmol) was added and the solution refluxed for 15 hours. The reaction mixture was allowed to cool to room temperature and then the yellow precipitate was filtered and washed with a small amount of methanol and diethyl ether. Yield: 0.319 g (83%). 1H NMR (400 MHz, MeOD-d$_4$): δ 8.85 (d, 2H), 8.26 (s, 2H), 8.16 (d, 2H), 5.51 (d, 0.8H), 4.98 (d, 0.2H), 4.44 (d, 1.2H), 3.93 (d, 2H), 3.55 (m, 2.2H), 2.98 (m, 1H), 2.84 (d, 1.4H), 1.90 (s, 1H), 1.84 (2.8H), 1.46 (s, 2.8). $^{19}$F{$^1$H} (400 MHz, MeOD-d$_4$, external stnd: KPF$_6$): δ −79.57. $^{31}${$^1$H} (400 MHz, MeOD-d$_4$, external stnd: KPF$_6$): −41.15, −45.58. IR (KBr, cm$^{-1}$): 3440 m, 3070 w, 2040 s, 1970 m, 1930 s, 1640 s, 1510 w, 1420 m, 1380 w, 1340 m, 1270 s, 1150 m, 1030 s, 989 m, 890 m, 867 m, 799 m, 705 w, 638 s, 551 m, 513 m, 469 w, 417 w. ESI-MS (pos. ion mode, ACN:H$_2$O 70:30 and 1% formic acid): m/z 708.13962 ([M]$^+$, calcd. 708.13801). Anal. Calcd. for (6) (C$_{27}$H$_{28}$F$_3$N$_5$O$_8$PReS): C, 37.85; H, 3.29; N, 8.17. Found: C, 38.02; H, 3.24; N, 8.09.

Synthesis of Re(CO)$_3$(bpy)(PTA) (7)

A mixture of Re(CO)$_3$(bpy)Cl (0.564 g, 1.22 mmol) and AgOTf (0.314 g, 1.22 mmol) in THF (123 mL) was refluxed at 75° C. for 3 hours in the dark. The white solid, AgCl precipitate, was removed via vacuum filtration. To the remaining yellow filtrate, 1, 3, 5-triaza-7-phosphaadamantane (PTA, 0.192 g, 1.22 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.523 g (59%). $^1$H NMR (400 MHz, MeOD-d$_4$): δ 9.13 (d, 2H), 8.74 (d, 2H), 8.40 (t, 2H), 7.81 (t, 2H), 4.42 (dd, 6H), 3.80 (s, 6H). $^{19}$F{$^1$H} (400 MHz, MeOD-d$_4$): δ −79.52. $^{31}$P{$^1$H} (400 MHz, MeOD-d$_4$, external stnd: KPF$_6$): −77.64. IR (KBr cm$^{-1}$): 3440 m, 2040 s, 1950 s, 1910 s, 1610 m, 1470 m, 1440 m, 1280 s, 1260 s, 1140 m, 1100 m, 1030 s, 1010 m, 969 m, 946 m, 903 w, 801 m, 770 s, 740 m, 631 s, 614 m, 587 m, 573 m, 512 m, 454 m. ESI-MS (pos. ion mode, ACN:H$_2$O 70:30 and 1% formic acid): m/z 584.08746 ([M]$^+$, calcd. 584.08558). Anal. Calcd. for (7) (C$_{20}$H$_{20}$F$_3$N$_5$O$_6$PReS): C, 32.79; H, 2.75; N, 9.56. Found: C, 32.51; H, 2.76; N, 9.38.

Synthesis of Re(CO)$_3$(bpy)(THP) (8)

A mixture of Re(CO)$_3$(bpy)Cl (0.100 g, 0.217 mmol) and AgOTf (0.056 g, 0.217 mmol) in THF (22 mL) was refluxed at 75° C. for 3 hours in the dark. Silver chloride was removed by vacuum filtration. The remaining yellow filtrate was further refluxed after the addition of tris(hydroxymethyl)phosphine (THP) (0.040 g, 0.326 mmol) for an additional 15 hours. The reaction mixture was allowed to cool to room temperature and then THF was removed by rotary evaporation, then dissolved in a minimal amount of methanol and filtered through celite. The crude yellow oil (0.170 g) was purified using preparatory RP-HPLC (CH$_3$OH/H$_2$O, 0-5 min (10% CH$_3$OH), 5-30 min (100% CH$_3$OH), 30-35 min (10% CH$_3$OH). Yield: 0.070 g (46%). 1H NMR (400 MHz, MeOD-d$_4$): δ 9.17 (d, 2H), 8.64 (d, 2H), 8.31 (t, 2H), 7.72 (t, 2H), 3.90 (s, 6H). $^{19}$F{$^1$H}(400 MHz, MeOD-d$_4$, external stnd: KPF$_6$): δ −79.34. $^{31}$P{$^1$H} (400 MHz, MeOD-d$_4$, external stnd: KPF$_6$): 2.50. IR (KBr cm$^{-1}$): 3433 s, 2874 m, 2038 s, 1930 s, 1915 s, 1681 s, 1633 s, 1473 m, 1450 m, 1181 s, 1030 m, 841 w, 769 m, 731 w, 534 w, 497 w, 417 m. ESI-MS (pos. ion mode, ACN:H$_2$O 70:30 and 1% formic acid): m/z 551.03927 ([M]$^+$, calcd. 551.03763). Anal. Calcd. for (8) (C18H$_{17}$F$_3$N$_2$O$_8$PRe): C, 32.58; H, 2.58; N, 4.22. Found: C, 31.68; H, 2.61; N, 4.09.

Synthesis of Re(CO)$_3$(bpy)(DAPTA) (9)

A mixture of Re(CO)$_3$(bpy)Cl (0.236 g, 0.51 mmol) and AgOTf (0.131 g, 0.51 mmol) in THF (55 mL) was refluxed at 75° C. for 3 hours in the dark. The white solid, AgCl precipitate, was removed via vacuum filtration. To the remaining yellow filtrate, 1,4-diacetyl-1,3,7-triaza-5-phosphabicylco[3.3.1]nonane (DAPTA, 0.150 g, 0.61 mmol) was added and the solution refluxed for 24 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.204 g (50%). $^1$H NMR (400 MHz, MeOD-d$_4$): δ 9.21 (t, 2H), 8.77 (d, 2H), 8.43 (t, 2H), 7.84 (t, 2H), 5.65 (d, 1H), 5.12 (d, 0.4H), 5.01 (d, 1H), 4.53 (d, 1H), 4.22 (m, 0.8H), 4.03 (d, 1H), 3.91 (d, 1H), 3.53 (d, 0.8H), 3.1 (d, 1.2H), 2.01 (s, 1H), 1.98 (s, 2.6H), 1.90 (s, 2.8H). $^{19}$F{$^1$H} (400 MHz, MeOD-d$_4$, external stnd: KPF$_6$): δ −79.56. $^{31}$P{$^1$H} (400 MHz, MeOD-d$_4$, external stnd: KPF$_6$): −44.42, −48.33. IR (KBr cm$^{-1}$): 3457 m, 2965 w, 2880 w, 2037 s, 1958 s, 1918 s, 1646 s, 1473 m, 1419 m, 1331 m, 1265 s, 1155 m, 1024 s, 987 m, 892 m, 776 m, 632 s, 515 m, 422 m. ESI-MS (pos. ion mode, ACN:H$_2$O 70:30 and 1% formic acid): m/z 656.10825 ([M]$^+$, calcd. 656.10671). Anal. Calcd. for (9).CH$_3$OH (C$_{24}$H$_{28}$F$_3$N$_5$O$_9$PReS): C, 34.45; H, 3.37; N, 8.37. Found: C, 35.17; H, 3.49; N, 8.38.

Synthesis of Re(CO)$_3$(dmbpy)(PTA) (10)

A mixture of Re(CO)$_3$(dmbpy)Cl (0.200 g, 0.43 mmol) and AgOTf (0.111 g, 0.43 mmol) in THF (47 mL) was refluxed at 75° C. for 3 hours in the dark. The white solid, AgCl precipitate, was removed via vacuum filtration. To the remaining yellow filtrate, 1, 3, 5-triaza-7-phosphaadamantane (PTA, 0.102 g, 0.65 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.254 g (77%). 1H NMR (400 MHz, MeOD-d$_4$): δ 8.91 (d, 2H), 8.60 (s, 2H), 7.62 (d, 2H), 4.42 (dd, 6H), 3.78 (s, 6H), 2.67 (s, 6H). $^{19}$F{$^1$H} (400 MHz, MeOD-d$_4$, external stnd: KPF$_6$): δ −79.53. $^{31}$P{$^1$H} (400 MHz, MeOD-d$_4$, external stnd: KPF$_6$): −77.22. IR (KBr cm$^{-1}$): 3452 m, 2940 w, 2033 s, 1951 s, 1921 s, 1626 w, 1266 s, 1139 w, 1031 m, 972 m, 948 m, 834 m, 801 m, 740 m, 637 s, 580 m, 500 m, 436 m. ESI-MS (pos. ion mode, ACN:H$_2$O 70:30 and 1% formic acid): m/z 612.11845 ([M]$^+$, calcd. 612.11743). Anal. Calcd. for (10) (C$_{22}$H$_{24}$F$_3$N$_5$O$_6$PReS): C, 34.74; H, 3.18; N, 9.21. Found: C, 34.97; H, 3.22; N, 9.11.

Synthesis of Re(CO)$_3$(dmbpy)(THP) (11)

A mixture of Re(CO)$_3$(dmbpy)Cl (0.200 g, 0.43 mmol) and AgOTf (0.111 g, 0.43 mmol) in THF (47 mL) was refluxed at 75° C. for 3 hours in the dark. Silver chloride was removed by vacuum filtration. The remaining yellow filtrate was further refluxed after the addition of tris(hydroxymethyl)phosphine (THP) (0.081 g, 0.65 mmol) for an additional 15 hours. The reaction mixture was allowed to cool to room temperature and then THF was removed by rotary evaporation. The crude yellow solid (0.307 g) was purified using preparatory RP-HPLC (CH$_3$OH/H$_2$O, 0-5 min (10% CH$_3$OH), 5-30 min (100% CH$_3$OH), 30-35 min (10% CH$_3$OH). Yield: 0.073 g (25%). $^1$H NMR (400 MHz, MeOD-d$_4$): δ 8.96 9d, 2H), 8.50 (s, 2H), 7.54 (d, 2H), 3.88 (s, 6H), 2.63 (s, 6H). 9F{$^1$H} (400 MHz, MeOD-d$_4$, external stnd: KPF$_6$): δ −76.36. $^{31}$P{$^1$H} (400 MHz, MeOD-d$_4$, external stnd: KPF$_6$): 3.26. IR (KBr cm$^{-1}$): 3404 m, 2900 w, 2031 s, 1935 s, 1920 s, 1675 m, 1621 w, 1440 w, 1200 m, 1130 m, 1035 m, 905 w, 830 m, 723 w, 637 w, 534 w, 508 m, 444 w. ESI-MS (pos. ion mode, ACN:H$_2$O 70:30 and 1% formic acid): n/z 579.07103 ([M]$^+$, calcd. 579.06893). Anal. Calcd. for (11) (C$_{20}$H$_{21}$F$_3$N$_2$O$_8$PReS): C, 32.79; H, 2.75; N, 9.56. Found: C, 32.51; H, 2.76; N, 9.38.

Synthesis of Re(CO)$_3$(dmbpy)(DAPTA) (12)

A mixture of Re(CO)$_3$(dmbpy)Cl (0.267 g, 0.57 mmol) and AgOTf (0.146 g, 0.57 mmol) in THF (65 mL) was refluxed at 75° C. for 3 hours in the dark. The white solid, AgCl, precipitate was removed via vacuum filtration. To the remaining yellow filtrate, 1,4-diacetyl-1,3,7-triaza-5-phosphabicylco[3.3.1]nonane (DAPTA, 0.211 g, 0.86 mmol) was added and the solution refluxed for 15 h. The reaction mixture was allowed to cool to room temperature and then the THF was removed using rotary evaporation. The yellow solid was then purified by dissolving in minimal amount of methanol, filtering through celite, and precipitating out a yellow solid with diethyl ether (repeated 2×). Yield: 0.194 g (41%). $^1$H NMR (400 MHz, MeOD-d$_4$): δ 8.99 (t, 2H), 8.63 (s, 2H), 7.65 (t, 2H), 5.64 (d, 0.8H), 5.13 (d, 0.2H), 5.00 (d, 0.8H), 4.54 (d, 1.6H), 4.22 (d, 0.8H), 4.04 (d, 1H), 3.89 (d, 1H), 3.56 (m, 0.6H), 3.12 (d, 1.2H), 2.68 (s, 6H), 2.02 (s, 1H), 1.98 (s, 2.6H), 1.91 (s, 2.8H). $^{19}$F{$^1$H} (400 MHz, MeOD-d$_4$, external stnd: KPF$_6$): δ −79.53. $^{31}$P{$^1$H} (400 MHz, MeOD-d$_4$, external stnd: KPF$_6$): −44.35, −47.93. IR (KBr cm$^{-1}$): 3433 m, 2038 s, 1943 s, 1924 s, 1648 m, 1420 m, 1333 w, 1262 m, 1156 w, 1030 m, 986 w, 890 w, 826 w, 782 w, 638 m, 500 w, 421 w. ESI-MS (pos. ion mode, ACN:H$_2$O 70:30 and 1% formic acid): n/z 684.13967 ([M]$^+$, calcd. 684.13801). Anal. Calcd. for (12).CH$_3$OH (C$_{26}$H$_{32}$F$_3$N$_5$O$_9$PReS): C, 36.11; H, 3.73; N, 8.10. Found: C, 36.31; H, 3.59; N, 8.19.

Synthesis of Re(CO)$_3$(dmobpy)(PTA) (13)

A mixture of Re(CO)$_3$(dmobpy)Cl (0.200 g, 0.38 mmol) and AgOTf (0.099 g, 0.38 mmol) in THF (47 mL) was refluxed at 75° C. for 3 hours in the dark. The white solid, AgCl precipitate, was removed via vacuum filtration. To the remaining yellow filtrate, 1, 3, 5-triaza-7-phosphaadamantane (PTA, 0.079 g, 0.50 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether (repeated 2x). Yield: 0.158 g (52%). $^1$H NMR (400 MHz, MeOD-d$_4$): δ 8.84 (d, 2H), 8.26 (s, 2H), 7.34 (d, 2H), 4.44 (dd, 6H), 4.14 (s, 6H), 3.80 (s, 6H). $^{19}$F{$^1$H} (400 MHz, MeOD-d$_4$, external stnd: KPF$_6$): δ −79.59. $^{31}$P{$^1$H} (400 MHz, MeOD-d$_4$, external stnd: KPF$_6$): −79.59. IR (KBr cm$^{-1}$): 3443 m, 2031 s, 1942 s, 1921 s, 1615 m, 1560 w, 1497 w, 1426 w, 1350 w, 1262 m, 1242 w, 1147 w, 1029 m, 974 w, 948 w, 899 w, 828 w, 801 w, 741 w, 636 m, 581 w, 514 w, 429 w. ESI-MS (pos. ion mode, ACN:H$_2$O 70:30 and 1% formic acid): m/z 644.10822 ([M]$^+$, calcd. 644.10671). Anal. Calcd. for (13) (C$_{22}$H$_{24}$F$_3$N$_5$O$_8$PReS): C, 33.33; H, 3.05; N, 8.84. Found: C, 33.39; H, 3.10; N, 8.80.

Synthesis of Re(CO)$_3$(dmobpy)(THP) (14)

A mixture of Re(CO)$_3$(dmobpy)Cl (0.297 g, 0.57 mmol) and AgOTf (0.146 g, 0.57 mmol) in THF (70 mL) was refluxed at 75° C. for 3 hours in the dark. Silver chloride was removed by vacuum filtration. The remaining yellow filtrate was further refluxed after the addition of tris(hydroxymethyl)phosphine (THP) (0.092 g, 0.74 mmol) for an additional 15 hours. The reaction mixture was allowed to cool to room temperature and then THF was removed by rotary evaporation, then dissolved in a minimal amount of methanol and filtered through celite. The crude yellow oil (0.439 g, 100%) was recrystallized using vapor diffusion of diethyl ether into a solution of methanol to afford yellow crystals. Yield: 0.030 g (7%). $^1$H NMR (400 MHz, MeOD-d$_4$): δ 8.88 (d, 2H), 8.16 (s, 2H), 7.27 (d, 2H), 4.10 (s, 6H), 3.90 (s, 6H). $^{19}$F{$^1$H} (400 MHz, MeOD-d$_4$, external stnd: KPF$_6$): δ −79.57. $^{31}$P{$^1$H} (400 MHz, MeOD-d$_4$, external stnd: KPF$_6$): 3.16. IR (KBr cm$^{-1}$): 3448 m, 2028 s, 1939 w, 1919 s, 1618 s, 1560 m, 1500 m, 1343 w, 1270 m, 1182 w, 1031 m, 905 w, 826 w, 639 w, 513 w, 434 w. ESI-MS (pos. ion mode, ACN:H$_2$O 70:30 and 1% formic acid): m/z 611.06037 ([M]$^+$, calcd. 611.05875). Anal. Calcd. for (14) (C$_{19}$H$_{21}$F$_3$N$_2$O$_{11}$PReS): C, 30.04; H, 2.79; N, 3.69. Found: C, 30.30; H, 2.79; N, 3.89.

Synthesis of Re(CO)$_3$(dmobpy)(DAPTA) (15)

A mixture of Re(CO)$_3$(dmobpy)Cl (0.210 g, 0.40 mmol) and AgOTf (0.103 g, 0.40 mmol) in THF (45 mL) was refluxed at 75° C. for 3 hours in the dark. The white solid, AgCl precipitate, was removed via vacuum filtration. To the remaining yellow filtrate, 1,4-diacetyl-1,3,7-triaza-5-phosphabicylco[3.3.1]nonane (DAPTA, 0.123 g, 0.52 mmol) was added and the solution refluxed for 15 hours. The reaction mixture was allowed to cool to room temperature and then the THF was removed using rotary evaporation. The yellow solid was then purified by dissolving in a minimal amount of methanol, filtering through celite, and precipitating out a yellow solid with diethyl ether. Yield: 0.343 g (99%). The solid material was recrystallized using vapor diffusion of diethyl ether into a solution of methanol to afford yellow crystals. Yield: 0.028 g. $^1$H NMR (400 MHz, MeOD-d$_4$): δ 8.91 (t, 2H), 8.29 (s, 2H), 7.37 (t, 2H), 5.67 (d, 0.8H), 5.15 (d, 0.4H), 5.02 (d, 1.2H), 4.56 (m, 1.5H), 4.22 (m, 1H), 4.15 (s, 6H), 4.05 (d, 0.8H), 3.92 (d, 0.8H), 3.54 (m, 2H), 3.14 (d, 1H), 2.03 (s, 1H), 1.99 (s, 2.4H), 1.92 (2.4H). $^{19}$F{$^1$H} (400 MHz, MeOD-d$_4$, external stnd: KPF$_6$): δ −79.57. $^{31}$P{$^1$H} (400 MHz, MeOD-d$_4$, external stnd: KPF$_6$): −43.34, −46.87. IR (KBr cm$^{-1}$): 3456 m, 2040 s, 1939 w, 1919 s, 1637 s, 1500 m, 1420 m, 1340 w, 1260 m, 1150 w, 1030 s, 889 w, 796 w, 638 m, 516 w, 419 m. ESI-MS (pos. ion mode, ACN:H$_2$O 70:30 and 1% formic acid): m/z 716.12966 ([M]$^+$, calcd. 716.12784). Anal. Calcd. for (15) (C$_{25}$H$_{28}$F$_3$N$_5$O$_{10}$PReS): C, 34.72; H, 3.26; N, 8.10. Found: C, 34.44; H, 3.50; N, 8.08.

In Vitro Anticancer Activities of the Re(I) Complexes

I. General Methods

HeLa (cervical cancer) cell line was cultured using Dulbecco's Modified Eagle's Medium (DMEM) supplemented with 10% fetal bovine serum (FBS). A2780 (ovarian cancer) and A2780CP70 (cisplatin-resistant ovarian cancer) cell lines were cultured as monolayers with Roswell Park Memorial Institute (RPMI)-1640 culture media supplemented with 10% fetal bovine serum. All cell lines were grown in a humidified incubator at 37° C. with an atmosphere of 5% CO$_2$. Cells were passed at 80-90% confluence, using trypsin/EDTA. Cells were tested monthly for *mycoplasma* contamination with the PlasmoTest™ *mycoplasma* detection kit from InvivoGen.

All compounds were dissolved in phosphate-buffered saline (PBS, pH 7.4) to prepare a 1-2 mM stock solution. For single dose studies, only HeLa cells were used. For both the single dose and full dose response, all cells were grown to 80-90% confluence, detached with trypsin/EDTA, seeded in 96-well plates at 2000 cells/well for HeLa cells and 4000 cells/well for A2780 and A2780CP70 cells in 100 μL of growth media, and incubated for 24 hours. The medium was removed and replaced with fresh medium (200 μL) containing a single concentration of a rhenium(I) complex or media. The cells were then incubated for 4 hours, and then the cells were dosed with 365 nm for 1 hour (one plate under the same dosing conditions was kept outside the incubator in the dark as a control). After exposure to light, the plates incubated for an additional 44 hours, the medium was removed from the wells, and (3(4,5-dimethylthiazol-2-yl)-2,5-tetrazolium bromide (MTT) in RPMI (200 μL, 1 mg/mL) was added. After 4 hours, the MTT/RPMI solution was removed, and the formazan crystals were dissolved in 200 μL of an 8:1 mixture of DMSO and pH 10 glycine buffer. The absorbance at 570 nm in each well was measured using a BioTek Synergy™ HT plate reader. Cell viability was determined by normalizing the absorbance of the treated wells to untreated wells. All compounds that had less than 50% cell viability were analyzed using a full dose response. The % viability data is an average of three independent experiments with six replicates per concentration. The same procedure was followed as above for the full dose response but instead, after 24 hours, varying concentrations of the desired compounds were added. Cell viability was again determined by normalizing the absorbance of the treated wells to untreated wells The concentration of the compound versus % viability was plotted to produce dose-response curves, which were analyzed using a logistic sigmoid function fit with MagicPlot Pro™ software. The reported IC$_{50}$ values are the average of three independent experiments with six replicates per concentration level.

II. In Vitro Anticancer Activities of [Re(CO)$_3$(N—N)(H$_2$O)][OTf] Complexes

The in vitro anticancer activities of these complexes were tested in human cervical cancer cells (HeLa), and the results are provided below in Table 1. The IC$_{50}$ values refer to the concentration at which cell proliferation is inhibited by 50%. The Hill-Slope is a quantitative measure of the steepness of the dose-response curve.

TABLE 1

In vitro anticancer activities of select rhenium(I) complexes

| Ligand (L-L) | IC$_{50}$ of Re—(H$_2$O) Complex (µM) | Hill Slope |
|---|---|---|
| (cisplatin) | 3.0 ± 1.2 | 0.87 ± 0.14 |
| bpy | 15 ± 5 | 2.0 ± 0.3 |
| 4,4'-dimethyl bpy | 5.8 ± 3.4 | 2.0 ± 0.8 |
| 4,4'-dimethoxy bpy | 8.8 ± 2.4 | 2.3 ± 0.9 |
| 4,4'dimethylester bpy | 210 ± 30 | 9.3 ± 4.6 |
| phen | 9.7 ± 5.8 | 4.8 ± 2.4 |
| 2,9-dimethyl phen | 0.97 ± 0.21 | 3.3 ± 0.7 |
| 4,7-diphenyl phen | 15 ± 7 | 0.86 ± 0.13 |

Of the above compounds tested, the [Re(CO)$_3$(N—N)(H$_2$O)][OTf] complex with N—N=2,9-dimethyl phen ligand exhibited the lowest IC$_{50}$, and hence, the greatest cytotoxicity. The Re complex containing the 2,9-dimethyl phen ligand was also tested in wild-type (KB) and cisplatin-resistant (KBCP20) cancer cells. The IC$_{50}$ values for cisplatin and [Re(CO)$_3$(N—N)(H$_2$O)][OTf] complex with N—N=2,9-dimethyl phen ligand are given in Table 2 below; the resistance factor (RF) is the ratio of the IC$_{50}$ values in cisplatin-resistant versus wild-type cell lines. As can be observed, the resistance factor for [Re(CO)$_3$(N—N)(H$_2$O)][OTf] complex with N—N=2,9-dimethyl phen ligand is significantly smaller than that for cisplatin, which indicates that this complex is able to circumvent cisplatin-resistance mechanisms.

TABLE 2

Comparative IC$_{50}$ values for cisplatin and [Re(CO)$_3$(N—N)(H$_2$O)][OTf] complex with N—N = 2,9-dimethyl phen ligand

|  | KB | KBCBP20 | RF |
|---|---|---|---|
| cisplatin | 0.8 | 50 | 62.5 |
| 2,9-dimethyl phen | 0.4 | 2.0 | 5 |

III. In Vitro Anticancer Activities of Phosphino-Re(I) Complexes

TABLE 3

| | Single Dose Cell Viability (%) | | IC$_{50}$ Value (µM) | |
|---|---|---|---|---|
| Compound | Dark | Light | Dark | Light |
| PTA-phen (1) | 99.4 ± 1.0 | 99.6 ± 0.7 | >200 | >200 |
| THP-phen (2) | 91.8 ± 8.7 | 2.5 ± 1.8 | >200 | 26.4 ± 9.2 |
| DAPTA-phen (3) | 93.3 ± 0.7 | 6.3 ± 0.6 | >200 | 5.9 ± 1.4 |
| PTA-dmphen (4) | 90.0 ± 8.8 | 87.0 ± 8.0 | | |
| THP-dmphen (5) | 61.8 ± 6.2 | 1.3 ± 1.1 | >200 | 9.6 ± 4.2 |
| DAPTA-dmphen (6) | 98.1 ± 3.3 | 5.6 ± 7.9 | >200 | 19.2 ± 2.9 |
| PTA-bpy (7) | 97.9 ± 3.7 | 90.5 ± 4.1 | | |
| THP-bpy (8) | 98.9 ± 1.6 | 73.1 ± 6.4 | | |
| DAPTA-bpy (9) | 97.1 ± 4.3 | 11.6 ± 10.1 | >200 | 14.9 ± 3.2 |
| PTA-dmbpy (10) | 94.4 ± 4.9 | 82.5 ± 9.7 | | |
| THP-dmbpy (11) | 93.3 ± 6.0 | 30.7 ± 14.6 | | |
| DAPTA-dmbpy (12) | 100.0 ± 0.6 | 19.6 ± 17.0 | >200 | 60.3 ± 18.2 |
| PTA-dmobpy (13) | 98.2 ± 3.2 | 96.0 ± 6.8 | | |
| THP-dmobpy (14) | 57.5 ± 11.0 | 12.7 ± 5.8 | 72.6 ± 23.2 | 68.0 ± 4.3 |
| DAPTA-dmobpy (15) | 76.6 ± 1.1 | 5.0 ± 7.0 | >200 | 26.4 ± 9.2 |

TABLE 4

| | IC$_{50}$ Value (µM) | | | | | |
|---|---|---|---|---|---|---|
| Compound | HeLa (dark) | HeLa (light) | A2780 (dark) | A2780 (light) | A2780CP70 (dark) | A2780CP70 (light) |
| PTA-phen (1) | >200 | >200 | >200 | 53.1 ± 2.6 | >200 | >200 |
| THP-phen (2) | >200 | 26.4 ± 9.2 | >200 | 4.6 ± 1.4 | >200 | 29.9 ± 7.7 |
| DAPTA-phen (3) | >200 | 5.9 ± 1.4 | >200 | 2.2 ± 1.1 | >200 | 3.2 ± 0.7 |
| DAPTA-phen dicarb (3b) | >200 | >200 | | | | |
| DAPTA-phen photoproduct (3c) | >200 | >200 | | | | |
| DAPTA-phen w/ oxyhemoglobin | >200 | >200 | | | | |

While there have been shown and described what are at present considered the preferred embodiments of the invention, those skilled in the art may make various changes and modifications which remain within the scope of the invention defined by the appended claims.

What is claimed is:

1. A composition comprising a rhenium(I) complex having the following structure:

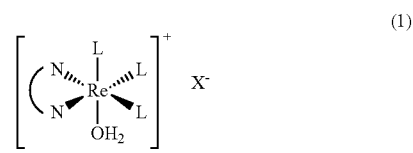

(1)

wherein Re represents a rhenium ion having a +1 charge;

represents an uncharged bidentate bicyclic ligand bonded to the rhenium (Re) by two ring nitrogen (N) atoms; and L is a neutral ligand independently selected from CO and neutral phosphine molecules, wherein at least one of the L groups is a CO molecule; and X⁻ represents a non-coordinating monovalent anion;
wherein:

is unsubstituted on any of its two rings, or

is substituted on at least one of its two rings with at least one of the following substituents: (i) hydrocarbon group (R) containing 1-6 carbon atoms; ii) —OR' groups; (iii) —C(O)OR' groups; (iv) —OC(O)R' groups; (v) —C(O)R' groups; (vi) —NR'₂ groups; (vii) —C(O)NR'₂ groups; (viii) —NR'C(O)R' groups; (ix) halogen atoms, and (x) —CN groups, wherein said hydrocarbon groups (R) optionally include one or more heteroatoms selected from oxygen, nitrogen, and sulfur, and R' is independently selected from hydrogen atoms and hydrocarbon groups (R);
wherein

has a bipyridyl, phenanthryl, or naphthyridyl core structure;
provided that, if

is bipyridyl, the bipyridyl is substituted with at least two groups selected from the group consisting of: (i) hydrocarbon groups (R) containing 1-6 carbon atoms, and (ii) —OR' groups; and
said neutral phosphine molecule either contains a phosphorus atom as a ring phosphorus atom or does not contain a phosphorus atom as a ring phosphorus atom;
provided that, if

is unsubstituted, then one or two of said L groups are selected from said neutral phosphine molecules, with the provision that at least one of the neutral phosphine molecules has a phosphorus atom as a ring phosphorus atom.

2. The composition of claim 1, wherein

has the following structure:

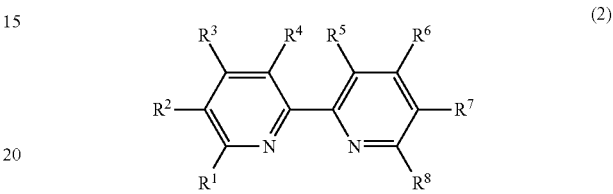

(2)

wherein $R^1$, $R^2$, $R^3$, $R^4$, $R^5$, $R^6$, $R^7$, and $R^8$ are independently selected from the group consisting of hydrogen atoms; hydrocarbon groups (R) containing 1-6 carbon atoms; and —OR' groups; and
wherein at least two of $R^1$, $R^2$, $R^3$, $R^4$, $R^5$, $R^6$, $R^7$, and $R^8$ are selected from the group consisting of: (i) hydrocarbon groups (R) containing 1-6 carbon atoms, and (ii) —OR' groups.

3. The composition of claim 2, wherein at least $R^3$ and $R^6$ and/or $R^1$ and $R^8$ are not hydrogen atoms.

4. The composition of claim 2, wherein at least $R^3$ and $R^6$ and/or $R^1$ and $R^8$ are selected from the group consisting of hydrocarbon groups (R) containing 1-6 carbon atoms; and —OR' groups.

5. The composition of claim 1, wherein

has the following structure:

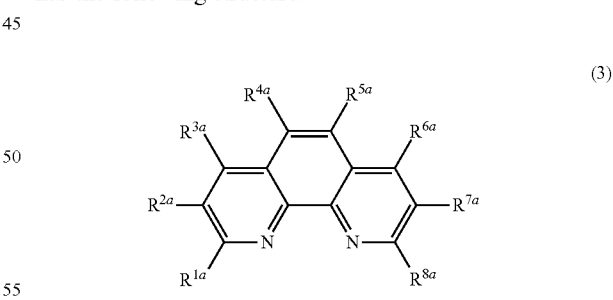

(3)

wherein $R^{1a}$, $R^{2a}$, $R^{3a}$, $R^{4a}$, $R^{5a}$, $R^{6a}$, $R^{7a}$, and $R^{8a}$ are independently selected from the group consisting of hydrogen atoms; hydrocarbon groups (R) containing 1-6 carbon atoms; —OR' groups; —C(O)OR' groups; —OC(O)R' groups; —C(O)R' groups; and halogen atoms, wherein said hydrocarbon groups (R) optionally include one or more heteroatoms selected from oxygen, nitrogen, and sulfur, and R' is independently selected from hydrogen atoms and hydrocarbon groups (R).

6. The composition of claim 5, wherein at least $R^{1a}$ and $R^{8a}$ and/or $R^{3a}$ and $R^{6a}$ are not hydrogen atoms.

7. The composition of claim 5, wherein at least $R^{1a}$ and $R^{8a}$ and/or $R^{3a}$ and $R^{6a}$ are selected from the group consisting of hydrocarbon groups (R) containing 1-6 carbon atoms; —OR' groups; —C(O)OR' groups; —OC(O)R' groups; and —C(O)R' groups.

8. The composition of claim 1, wherein

has the following structure:

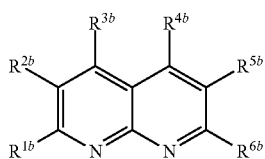

(4)

wherein $R^{1b}$, $R^{2b}$, $R^{3b}$, $R^{4b}$, $R^{5b}$, and $R^{6b}$ are independently selected from the group consisting of hydrogen atoms; hydrocarbon groups (R) containing 1-6 carbon atoms; —OR' groups; —C(O)OR' groups; —OC(O)R' groups; —C(O)R' groups; and halogen atoms, wherein said hydrocarbon groups (R) optionally include one or more heteroatoms selected from oxygen, nitrogen, and sulfur, and R' is independently selected from hydrogen atoms and hydrocarbon groups (R).

9. The composition of claim 8, wherein at least $R^{1b}$ and $R^{6b}$ and/or $R^{3b}$ and $R^{4b}$ are not hydrogen atoms.

10. The composition of claim 8, wherein at least two of $R^{1b}$, $R^{2b}$, $R^{3b}$, $R^{4b}$, $R^{5b}$, and $R^{6b}$ are independently selected from the group consisting of hydrocarbon groups (R) containing 1-6 carbon atoms; —OR' groups; —C(O)OR' groups; —OC(O)R' groups; and —C(O)R' groups.

11. The composition of claim 8, wherein at least $R^{1b}$ and $R^{6b}$ and/or $R^{3b}$ and $R^{4b}$ are selected from the group consisting of hydrocarbon groups (R) containing 1-6 carbon atoms; —OR' groups; —C(O)OR' groups; —OC(O)R' groups; and —C(O)R' groups.

12. The composition of claim 1, wherein said non-coordinating monovalent anion is selected from $SO_3CF_3^-$, $PF_6^+$, tosylate, $SbF_6^-$, borate anions, $AsF_6^-$, $ClO_4^-$, and carborane anions.

13. The composition of claim 1, wherein said rhenium(I) complex is dispersed in a pharmaceutically acceptable carrier.

14. A method for treating cancer in a subject, the method comprising administering to said subject a pharmaceutically effective amount of a rhenium(I) complex having the following structure:

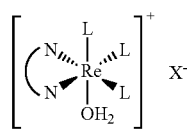

(1)

wherein Re represents a rhenium ion having a +1 charge;

represents an uncharged bidentate bicyclic ligand bonded to the rhenium (Re) by two ring nitrogen (N) atoms; and L is a neutral ligand independently selected from CO and neutral phosphine molecules, wherein at least one of the L groups is a CO molecule; and $X^-$ represents a non-coordinating monovalent anion;
wherein:

is unsubstituted on any of its two rings, or

is substituted on at least one of its two rings with at least one of the following substituents: (i) hydrocarbon groups (R) containing 1-6 carbon atoms; ii) —OR' groups; (iii) —C(O)OR' groups; (iv) —OC(O)R' groups; (v) —C(O)R' groups; (vi) —NR'$_2$ groups; (vii) —C(O)NR'$_2$ groups; (viii) —NR'C(O)R' groups; (ix) halogen atoms, and (x) —CN groups, wherein said hydrocarbon groups (R) optionally include one or more heteroatoms selected from oxygen, nitrogen, and sulfur, and R' is independently selected from hydrogen atoms and hydrocarbon groups (R);
wherein

has a bipyridyl, phenanthryl, or naphthyridyl core structure; provided that, if

is bipyridyl, the bipyridyl is substituted with at least two groups selected from the group consisting of: (i) hydrocarbon groups (R) containing 1-6 carbon atoms, and (ii) —OR' groups; and
said neutral phosphine molecule either contains a phosphorus atom as a ring phosphorus atom or does not contain a phosphorus atom as a ring phosphorus atom; provided that, if

is unsubstituted, then one or two of said L groups are selected from said neutral phosphine molecules, with the provision that at least one of the neutral phosphine molecules has a phosphorus atom as a ring phosphorus atom;

and wherein said cancer is selected from cervical, ovarian, and cisplatin-resistant cancer.

15. The method of claim 14, wherein said cancer is a cisplatinum-resistant cancer.

16. The method of claim 14, wherein

has the following structure:

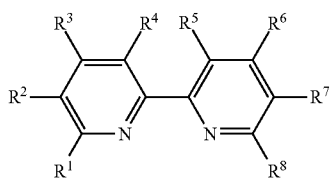

(2)

wherein $R^1$, $R^2$, $R^3$, $R^4$, $R^5$, $R^6$, $R^7$, and $R^8$ are independently selected from the group consisting of hydrogen atoms; hydrocarbon groups (R) containing 1-6 carbon atoms; and —OR' groups; and wherein at least two of $R^1$, $R^2$, $R^3$, $R^4$, $R^5$, $R^6$, $R^7$, and $R^8$ are selected from the group consisting of: (i) hydrocarbon groups (R) containing 1-6 carbon atoms, and (ii) —OR' groups.

17. The method of claim 16, wherein at least $R^3$ and $R^6$ and/or $R^1$ and $R^8$ are not hydrogen atoms.

18. The method of claim 16, wherein at least $R^3$ and $R^6$ and/or $R^1$ and $R^8$ are selected from the group consisting of hydrocarbon groups (R) containing 1-6 carbon atoms; and —OR' groups.

19. The method of claim 14, wherein

has the following structure:

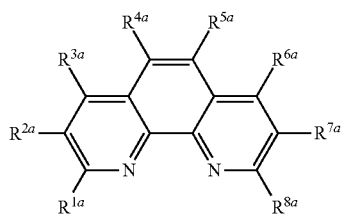

(3)

wherein $R^{1a}$, $R^{2a}$, $R^{3a}$, $R^{4a}$, $R^{5a}$, $R^{6a}$, $R^{7a}$, and $R^{8a}$ are independently selected from the group consisting of hydrogen atoms; hydrocarbon groups (R) containing 1-6 carbon atoms; —OR' groups; —C(O)OR' groups; —OC(O)R' groups; —C(O)R' groups; and halogen atoms, wherein said hydrocarbon groups (R) optionally include one or more heteroatoms selected from oxygen, nitrogen, and sulfur, and R' is independently selected from hydrogen atoms and hydrocarbon groups (R).

20. The method of claim 19, wherein at least $R^{1a}$ and $R^{8a}$ and/or $R^{3a}$ and $R^{6a}$ are not hydrogen atoms.

21. The method of claim 19, wherein at least $R^{1a}$ and $R^{8a}$ and/or $R^{3a}$ and $R^{6a}$ are selected from the group consisting of hydrocarbon groups (R) containing 1-6 carbon atoms; —OR' groups; —C(O)OR' groups; —OC(O)R' groups; and —C(O)R' groups.

22. The method of claim 14, wherein

has the following structure:

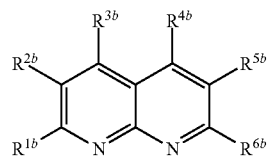

(4)

wherein $R^{1b}$, $R^{2b}$, $R^{3b}$, $R^{4b}$, $R^{5b}$, and $R^{6b}$ are independently selected from the group consisting of hydrogen atoms; hydrocarbon groups (R) containing 1-6 carbon atoms; —OR' groups; —C(O)OR' groups; —OC(O)R' groups; —C(O)R' groups; and halogen atoms, wherein said hydrocarbon groups (R) optionally include one or more heteroatoms selected from oxygen, nitrogen, and sulfur, and R' is independently selected from hydrogen atoms and hydrocarbon groups (R).

23. The method of claim 22, wherein at least $R^{1b}$ and $R^{6b}$ and/or $R^{3b}$ and $R^{4b}$ are not hydrogen atoms.

24. The method of claim 22, wherein at least two of $R^{1b}$, $R^{2b}$, $R^{3b}$, $R^{4b}$, $R^{5b}$, and $R^{6b}$ are independently selected from the group consisting of hydrocarbon groups (R) containing 1-6 carbon atoms; —OR' groups; —C(O)OR' groups; —OC(O)R' groups; and —C(O)R' groups.

25. The method of claim 22, wherein at least $R^{1b}$ and $R^{6b}$ and/or $R^{3b}$ and $R^{4b}$ are selected from the group consisting of hydrocarbon groups (R) containing 1-6 carbon atoms; —OR' groups; —C(O)OR' groups; —OC(O)R' groups; and —C(O)R' groups.

26. The method of claim 14, wherein said non-coordinating monovalent anion is selected from $SO_3CF_3^-$, $PF_6^-$, tosylate, $SbF_6^-$, borate anions, $AsF_6^-$, $ClO_4^-$, and carborane anions.

27. A composition comprising a rhenium(I) complex having the following structure:

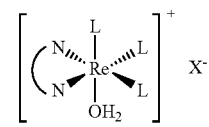

(1)

wherein Re represents a rhenium ion having a +1 charge;

represents an uncharged bidentate bicyclic ligand bonded to the rhenium (Re) by two ring nitrogen (N) atoms, wherein

is unsubstituted on any of its two rings, or

is substituted on at least one of its two rings with at least one of the following substituents: (i) hydrocarbon group (R) containing 1-6 carbon atoms; ii) —OR' groups; (iii) —C(O)OR' groups; (iv) —OC(O)R' groups; (v) —C(O)R' groups; (vi) —NR'$_2$ groups; (vii) —C(O)NR'$_2$ groups; (viii) —NR'C(O)R' groups; (ix) halogen atoms, and (x) —CN groups, wherein said hydrocarbon groups (R) optionally include one or more heteroatoms selected from oxygen, nitrogen, and sulfur, and R' is independently selected from hydrogen atoms and hydrocarbon groups (R);

L$^1$ is a neutral cyclic phosphine molecule containing a ring phosphorus atom;

L$^2$ and L$^3$ are CO molecules; and

X$^-$ represents a non-coordinating monovalent anion.

28. The composition of claim 27, wherein the neutral cyclic phosphine molecule is

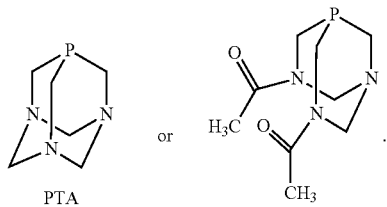

* * * * *

UNITED STATES PATENT AND TRADEMARK OFFICE
CERTIFICATE OF CORRECTION

| | | |
|---|---|---|
| PATENT NO. | : 10,973,849 B2 | |
| APPLICATION NO. | : 16/311961 | |
| DATED | : April 13, 2021 | |
| INVENTOR(S) | : Justin Wilson, Kevin Knopf and Sierra Marker | |

It is certified that error appears in the above-identified patent and that said Letters Patent is hereby corrected as shown below:

In the Specification

Column 1, Line 10, insert:
--U.S. GOVERNMENT SUPPORT
This invention was made with government support under Grant No. W81XWH-17-1-0097 awarded by the U.S. Army Medical Research and Materiel Command. The government has certain rights in the invention--

Signed and Sealed this
Sixteenth Day of July, 2024

*Katherine Kelly Vidal*

Katherine Kelly Vidal
*Director of the United States Patent and Trademark Office*